United States Patent
Paniagua-Solís et al.

(10) Patent No.: US 9,399,677 B2
(45) Date of Patent: Jul. 26, 2016

(54) V$_H$NAR ANTI-CYTOKINE DOMAINS

(71) Applicant: Laboratorios Silanes, S.A. de C.V., Mexico, D.F. (MX)

(72) Inventors: Jorge F. Paniagua-Solís, México, D.F. (MX); María Teresa Mata-González, México, D.F. (MX); Walter J. García-Ubbelohde, México, D.F. (MX); Araceli Olguín-Jimenez, México, D.F. (MX); Alexei F. Licea-Navarro, Ensenada, BC (MX); Tanya A. Camacho-Villegas, Ensenada, BC (MX); Edna Sanchez-Castrejon, Ensenada, BC (MX)

(73) Assignee: LABORATORIES SILANES S.A. DE C.V., Delegacion Benito Juarez (MX)

( * ) Notice: Subject to any disclaimer, the term of this patent is extended or adjusted under 35 U.S.C. 154(b) by 0 days.

(21) Appl. No.: 13/944,522

(22) Filed: Jul. 17, 2013

(65) Prior Publication Data

US 2014/0044716 A1 Feb. 13, 2014

Related U.S. Application Data

(63) Continuation of application No. 12/939,195, filed on Nov. 4, 2010, now Pat. No. 8,496,933.

(60) Provisional application No. 61/258,118, filed on Nov. 4, 2009.

(51) Int. Cl.
*A61K 39/395* (2006.01)
*A61K 38/16* (2006.01)
*C07K 16/22* (2006.01)
*C07K 16/24* (2006.01)
*A61K 39/00* (2006.01)

(52) U.S. Cl.
CPC .............. *C07K 16/241* (2013.01); *C07K 16/22* (2013.01); *A61K 2039/505* (2013.01); *C07K 2317/20* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS 8,496,933 B2  7/2013  Paniagua-Solis et al.
8,865,431 B2  10/2014 Dooley et al.

FOREIGN PATENT DOCUMENTS

WO  WO 2005/118629 A1  12/2005

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Adelaida Echeverri Montaño, M., et al., "New advances in biologic therapy of psoriasis," *Med. Cutan. Iber. Lat. Am.* 33(1): 7-17, Galderma S.A., Spain (2005).
Angus, D.C., et al., "Epidemiology of severe sepsis in the United States: Analysis of incidence, outcome, and associated costs of care," *Crit. Care Med* 29: 1303-1310, Lippincott Williams & Wilkins, United States (2001).
Bochud, P.-Y. & Calandra, T., "Pathogenesis of sepsis: new concepts and implications for future treatment," *BMJ* 326: 262-266, BMJ Publishing Group, United States (2003).
Coleman, H.R., et al., "Age-related macular degeneration," *Lancet* 372(9652): 1835-1845, Elsevier Ltd., United Kingdom (2008).
De Gannes, G.C., et al., "Psoriasis Pustular Dermatitis Triggered by TNF-α Inhibitors in Patients With Rheumatologic Conditions," *Arch. Dermatol.* 143(2):223-231, American Medical Association, United States (2007).
Diaz, M., et al., "Mutational pattern of the nurse shark antigen receptor gene (NAR) is similar to that of mammalian Ig genes and to spontaneous mutations in evolution: the translesion synthesis model of somatic hypermutation," *International Immunology* 11(5): 825-833, The Japanese Society for Immunology, Japan (1999).
Dooley, H., et al., "Selection and characterization of naturally occuring single-domain (IgNAR) antibody fragments from immunized sharks by phage display," *Mol. Immunol.* 40(1): 25-33, Elsevier Ltd., United Kingdom (2003).
Dumoulin, M., et al., "Single-domain antibody fragments with high conformational stability," *Protein Science* 11: 500-515, Cold Spring Harbor Laboratory Press, United States (2002).
Durán Giménez-Rico, H.J., et al., "Sepsis shock séptico: un torbellino de mediadores inflamatorios de dfficil manejo terapéutico," *An. Med. Interna.* 19(1): 35-43, Aran Ediciones, S.L., Spain (2002).
Ebong, S., et al., "Immunopathologic Alterations in Murine Models of Sepsis of Increasing Severity," *Infect. Immu.* 67: 6603-6610, American Society for Microbiology, United States (1999).

(Continued)

*Primary Examiner* — Christine J Saoud
*Assistant Examiner* — Jon M Lockard
(74) *Attorney, Agent, or Firm* — Sterne, Kessler, Goldstein & Fox P.L.L.C.

(57) ABSTRACT

The present invention concerns therapeutic compositions containing proteins that are the variable regions of IgNAR immunoglobulins, denominated vNAR, that specifically bind and neutralizes cytokines involved in a diversity of process such as inflammation and neovascularization, its ability to reach, bind, and neutralize the activity of one antigenic molecule localized in an immunoprivileged organs, are also described.

33 Claims, 7 Drawing Sheets

(56) References Cited

OTHER PUBLICATIONS

Feldmann, M. & Maini, R.N., "Anti-TNFα Therapy of Rheumatoid Arthritis: What Have We Learned?" *Annual Review of Immunology* 19: 163-196, Annual Reviews, United States (2001)

Gérard, C., et al., "Interleukin 10 Reduces the Release of Tumor Necrosis Factor and Prevents Lethality in Experimental Endotoxemia," *J. Exp. Med.* 177: 547-550, The Rockefeller University Press, United States (1993).

Green, R.S., et al., "Canadian Association of Emergency Physicians Sepsis Guidelines: the optimal management of severe sepsis in Canadian emergency departments," *CJEM* 10(5):443-459, JCMU, Canada (2008).

Hendriksen, E.M., et al., "Angiogenesis, hypoxia and VEGF expression during tumour growth in a human xenograft tumour model," *Microvascular Research* 77: 96-103, Elsevier, United Kingdom (2009).

Maharaj, A.S.R. & D'Amore, P.A., "Roles for VEGF in adult," *Microvasc. Res.* 74(2-3): 100-113, Elsevier Inc., United Kingdom (2007).

Muyldermans, S. & Lauwereys, M., "Unique single-domain antigen binding fragments derived from naturally occurring camel heavy-chain antibodies," *Journal of Molecular Recognition* 12: 131-140, John Wiley & Sons, Ltd., United States (1999).

Nuttall, S.D., et al., "A naturally occurring NAR variable domain binds the Kgp protease from *Porphyromonas gingivalis*," *FEBS Lett.* 516(1-3): 80-86, Elsevier Science B.V., United Kingdom (2002).

Nuttall, S.D., et al., "Isolation and characterization of an IgNAR variable domain specific for the human mitochondrial translocase receptor Tom70," *Eur. J. Biochem* 270: 3543-3554, FEBS, United Kingdom (2003).

Nuttall, S.D., et al., "Isolation of the new antigen receptor from wobbegong sharks, and use as a scaffold for the display of protein loop libraries," *Mol. Immunol.* 38(4): 313-326, Elsevier Science Ltd., United Kingdom (2001).

Nuttall, S.D., et al, "Selection and Affinity Maturation of IgNAR Variable Domains Targeting *Plasmodium falciparum* AMA1," *Proteins* 55(1): 187-197, Wiley-Liss, Inc., United States (2004).

Stone, J., et al., "Development of Retinal Vasculature is Mediated by Hypoxia-Induced Vascular Endothelial Growth Factor (VEGF) Expression by Neuroglia," *J. Neurosci.* 15 (7 Pt 1): 4738-4747, Society for Neuroscience, United States (1995).

Wenzel, R.P., et al., "Current Understanding of Sepsis," *CID* 22: 407-413, The University of Chicago, United States (1996).

Witmer, A.N., et al., "Vascular endothelial growth factors and angiogenesis in eye disease," *Prog. Retin. Eye Res.* 22(1): 1-29, Elsevier Science Ltd., United Kingdom (2003).

Camacho Villegas, T.A., "Isolation of Single Domain Antibodies $V_HNAR$ from the Shark *Heterodonuts francisci* Able to Neutralize the Cytokines TNF-α and $VEGF_{165}$," Master's Thesis, Centro de Investigación Cientifica y de Educación Superior de Ensenada, Ensenada, Baja California, México (English translation of original)(Feb. 27, 2009).

Dooley, H. and Flajnik, M.F., "Antibody repertoire development in cartilaginous fish," *Dev. Comp. Immunol.*, 30:42-56, Elsevier Ltd., Amsterdam, Netherlands (available online Jul. 2005).

Wesolowski, J., et al., "Single domain antibodies: promising experimental and therapeutic tools in infection and immunity," *Med. Microbiol. Immunol.* 198:157-174, Springer-Verlag, Berlin, Germany (Jun. 2009).

International Search Report for International Appl. No. PCT/MX2010/000122, filed Nov. 4, 2010, Oficina Española de Patentes y Marcas, Madrid, Spain, Dated: Jul. 12, 2011.

Non-Final Office Action mailed Dec. 14, 2012 for U.S. Appl. No. 12/939,195, filed Nov. 4, 2010.

* cited by examiner

FIGURE 1

Formatted Alignments

```
              10                  20                    30
TNF43  A S L D Q T L R T A T R E T G E S L T V N C V L V D A I Y G
TNF65  A S L D Q T P R T A T R E T G E S L T V N C V L V D A N Y G
       A S L D Q T   R T A T R E T G E S L T V N C V L V D A   Y G 40                  50                    60
TNF43  L Y S T S W Y R N N P G S T D R E H I T I G G R Y V E S V N
TNF65  L Y N T S W Y R N N P G S T D R E H I T I G G R Y V E S V N
       L Y   T S W Y R N N P G S T D R E H I T I G G R Y V E S V N 70                  80                    90
TNF43  K G A K S F S L Q I K D M T F E D S G T Y Y C K A R . . . .
TNF65  K G A K S F S L Q I K D M T V E D S G T Y Y C K A R E S D Y
       K G A K S F S L Q I K D M T   E D S G T Y Y C K A R E S D Y 100                 110                   120
TNF43  . . . A T S G T T P H D G S G T V L T V N    SEQ ID NO:1
TNF65  N R V G I R D I K D Y D G A G T V L T V N    SEQ ID NO:3
       N R V .       Y     D G   G T V L T V N
```

Protector effect of 0.5ug/mL and 0.1ug/mL doses compared with placebo on the endothelial cells proliferation of the retina.
* vs placebo p=0.00
**vs placebo p=0.03
Anova test post-hoc Bonferroni.

SEQUENCE LISTING

<160> NUMBER OF SEQ ID NOS: 16

<210> SEQ ID NO 1
<211> LENGTH: 104
<212> TYPE: PRT
<213> ORGANISM: Heterodontud francisi

<400> SEQUENCE: 1

Ala Ser Leu Asp Gln Thr Leu Arg Thr Ala Thr Arg Glu Thr Gly Glu
1               5                   10                  15

Ser Leu Thr Val Asn Cys Val Leu Tyr Asp Ala Asn Tyr Gly Leu Tyr
            20                  25                  30

Ser Thr Ser Trp Tyr Arg Asn Asn Pro Gly Ser Thr Asp Arg Glu His
        35                  40                  45

Ile Thr Ile Gly Gly Arg Tyr Val Glu Ser Val Asn Lys Gly Ala Lys
    50                  55                  60

Ser Phe Ser Leu Gln Ile Lys Asp Met Thr Val Glu Asp Ser Gly Thr
65                  70                  75                  80

Tyr Tyr Cys Lys Ala Arg Ala Thr Ser Gly Tyr Thr Pro His Asp Gly
                85                  90                  95

Ser Gly Thr Val Leu Thr Val Asn
            100

<210> SEQ ID NO 2
<211> LENGTH: 309
<212> TYPE: DNA
<213> ORGANISM: Heterodontus francisci

<400> SEQUENCE: 2
gcaagcctgg accaaacaca agaacggcac gagagaaaca ggcgaatcgc ctgaccgtta      60
actgcgtcct cgttgatgct atctatggtt tgtacagcac atcttggtac cgcaataatc     120
cgggttcaac agacagggaa cacataacga ttggcggacg atatgttgaa tcagtcaaca     180
aaggagcaaa gtcatttcct ctgcaaatca aggacatgac atttgaagac agtggcacct     240
attactgcaa agcgcgatac atctgggtat accccccacg acggatctgg caccgtgctg     300
actgtgaac                                                             309

<210> SEQ ID NO 3
<211> LENGTH: 111
<212> TYPE: PRT
<213> ORGANISM: Heterodontus francisi

<400> SEQUENCE: 3

Ala Ser Leu Asp Gln Thr Pro Arg Thr Ala Thr Arg Glu Thr Gly Glu
1               5                   10                  15

Ser Leu Thr Val Asn Cys Val Leu Val Asp Ala Asn Tyr Gly Leu Tyr
            20                  25                  30

Asn Thr Ser Trp Tyr Arg Asn Asn Pro Gly Ser Thr Asp Arg Glu His
        35                  40                  45

Ile Thr Ile Gly Gly Arg Tyr Val Glu Ser Val Asn Lys Gly Ala Lys
    50                  55                  60

Ser Phe Ser Leu Gln Ile Lys Asp Met Thr Val Glu Asp Ser Gly Thr
65                  70                  75                  80

Tyr Tyr Cys Lys Ala Arg Glu Ser Asp Tyr Asn Arg Val Gly Ile Arg
                85                  90                  95

Asp Tyr Lys Asp Tyr Asp Gly Ala Gly Thr Val Leu Thr Val Asn
            100                 105                 110

<210> SEQ ID NO 4
<211> LENGTH: 334
<212> TYPE: DNA
<213> ORGANISM: Heterodontus francisi

<400> SEQUENCE: 4

```
gcaagcctgg accaaacacc aagaacggca acgagagaga caggcgaatc cctgaccgtt    60
aactgcgtcc cgttgatgct aactatggtt tgtacaacac atcttggtac cgcaataatc   120
cgggttcaac agacagggaa cacataacga ttggcggacg atatgttgaa tcagtcaaca   180
aaggagcaaa gtcattttct ctgcaaatca aggacatgac agttgaagac agtggcacct   240
attactgcaa agcgcgagag agcgactaca atagggtagg tatacgggac tacaaggact   300
acgacggagc tggcaccgtg ctgactgtga acgg                                334
```

<210> SEQ ID NO 5
<211> LENGTH: 122
<212> TYPE: PRT
<213> ORGANISM: Heterodontus francisi

<400> SEQUENCE: 5

```
Ala Ser Leu Asp Gln Thr Pro Arg Ala Thr Arg Glu Thr Gly Glu Ser
1               5                  10                  15
Leu Ser Ile Asn Cys Val Leu Thr Asp Thr Ser His Ile Leu Phe Gly
            20                  25                  30
Thr Lys Trp Leu Trp Asn Asn Pro Gly Ser Thr Asp Trp Glu Ile Ser
        35                  40                  45
Thr Ile Gly Gly Arg Tyr Ala Glu Ser Val Asn Asn Gln Ala Lys Ser
    50                  55                  60
Phe Ser Leu Gln Ile Lys Asp Leu Thr Val Glu Asp Ser Gly Thr Tyr
65                  70                  75                  80
Tyr Cys Lys Ala Gln Thr Ile Gly Arg Arg Lys Asn Leu Leu Pro Arg
                85                  90                  95
Pro Leu Val Asn Gly Ile Ala Ala Met Gly Tyr Ser Ser Ser Asp Tyr
            100                 105                 110
Asp Gly Ala Gly Thr Val Leu Thr Val Asn
        115                 120
```

<210> SEQ ID NO 6
<211> LENGTH: 434
<212> TYPE: DNA
<213> ORGANISM: Heterodontus francisi

<400> SEQUENCE: 6

```
gcaagcctgg accaaacacc aagaacggca acgagagaga caggcgaatc cctgagcatt    60
aactgcgtcc tcactgatac tagccatatt tgttcggca caaatggct ctggaataat    120
ccgggttcaa cagattggga agcataacg attggcggac gatatgctga atcagtcaac    180
aaccaagcaa agtcattttc tctgcaaatc aaggacctga cagttgaaga cagtggcacc    240
tattactgca aagcgcaaac cataggaaga cgcaaaaatc tacttccacg ccattggtga    300
acggtatagc tgcaaagcgc aaaccatagg aagacgcaaa atcttactt ccacgcccat    360
tggtgaacgg tatagctgcg atggggtata gctccagtga ctacgacgga gctggcaccg    420
tgctgactgt gaac                                                      434
```

<210> SEQ ID NO 7

```
<211> LENGTH: 127
<212> TYPE: PRT
<213> ORGANISM: Heterodontus francisi

<400> SEQUENCE: 7

Ala Ser Leu Asp Gln Thr Leu Arg Thr Ala Thr Arg Glu Thr Gly Glu
1               5                   10                  15

Ser Leu Thr Val Asn Cys Val Leu Val Asp Ala Asn Tyr Gly Leu Tyr
                20                  25                  30

Ser Thr Ser Trp Tyr Arg Asn Asn Pro Gly Ser Thr Asp Arg Glu His
            35                  40                  45

Ile Thr Ile Gly Gly Arg Tyr Val Glu Ser Val Asn Lys Gly Ala Lys
        50                  55                  60

Ser Phe Ser Leu Gln Ile Lys Asp Met Thr Val Glu Asp Ser Gly Thr
65                  70                  75                  80

Tyr Tyr Cys Lys Ala Arg Ala Thr Ser Gly Tyr Thr Pro His Asp Gly
                85                  90                  95

Ala Gly Thr Val Leu Thr Val Asn Ser Leu Gln Lys Leu Ile Ser
            100                 105                 110

Glu Glu Asp Leu Asn Ser Ala Val Asp His His His His His His
        115                 120                 125

<210> SEQ ID NO 8
<211> LENGTH: 439
<212> TYPE: DNA
<213> ORGANISM: Heterodontus francisi

<400> SEQUENCE: 8
gcaagcctgg accaaacact aagaacggca acgagagaga caggcgaatc cctgaccgtt      60
aactgcgtcc tcgttgatgc taactatggt ttgtacagca catcttggta ccgcaataat     120
ccgggttcaa cagacaggga acacataacg attggcggac gatatgttga atcagtcaac     180
aaaggagcaa agtcattttc tctgcaaatc aaggacatga cagttgaaga cagtggcacc     240
tattactgca agcgcgagc tacatctggg tatacccccc acgacggagc tggcacctat     300
tactgcaaag cgcgagctac atctgggtat acccccacg acggagctgg caccgtgctg     360
actgtgaact ctagaacaaa aactcatctc agaagaggat ctgaatagcg ccgtcgacca     420
tcatcatcat catcattga                                                 439

<210> SEQ ID NO 9
<211> LENGTH: 127
<212> TYPE: PRT
<213> ORGANISM: Heterodontus francisi

<400> SEQUENCE: 9

Ala Ser Leu Asp Gln Thr Leu Arg Thr Ala Thr Arg Glu Thr Gly Glu
1               5                   10                  15

Ser Leu Thr Val Asn Cys Val Leu Val Asp Ala Asn Tyr Gly Leu Tyr
                20                  25                  30

Ser Thr Ser Trp Tyr Arg Asn Asn Pro Gly Ser Thr Asp Arg Glu His
            35                  40                  45

Ile Thr Ile Gly Gly Arg Tyr Val Glu Ser Val Asn Lys Gly Ala Lys
        50                  55                  60

Ser Phe Ser Leu Gln Ile Lys Asp Met Thr Val Glu Asp Ser Gly Thr
65                  70                  75                  80

Tyr Tyr Cys Lys Ala Arg Ala Thr Ser Gly Tyr Thr Pro His Asp Gly
                85                  90                  95
```

Ala Gly Thr Val Leu Thr Val Asn Gly Gln Ala Gly Gln His His His
            100                 105                 110

His His His Gly Ala Tyr Pro Tyr Asp Val Pro Asp Tyr Ala Ser
            115                 120                 125

<210> SEQ ID NO 10
<211> LENGTH: 378
<212> TYPE: DNA
<213> ORGANISM: Heterodontus francisi

<400> SEQUENCE: 10
gcaagcctgg accaaacact aagaacggca acgagagaca ggcgaatccc tgaccgttaa      60
ctgcgtcctc gttgatgcta actatggttt gtacagcaca tcttggtacc gcaataatcc    120
gggttcaaca gacagggaac acataacgat tggcggacga tatgttgaat cagtcaacaa    180
aggagcaaag tcattttctc tgcaaatcaa ggacatgaca gttgaagaca gtggcaccta    240
ttactgcaaa gcgcgagcta catctgggta taccccccac gacggagctg gcaccgtgct    300
gtgaacggcc aggccggcca gcaccatcac catcatcacg gcgcataccc gtacgacgtt    360
ccggactacg cttcttag                                                  378

<210> SEQ ID NO 11
<211> LENGTH: 26
<212> TYPE: DNA
<213> ORGANISM: Artificial Sequence
<220> FEATURE:
<223> OTHER INFORMATION: Antisense oligonucleotide

<400> SEQUENCE: 11
gttcacagtc agcacggtgc cagctc                                          26

<210> SEQ ID NO 12
<211> LENGTH: 20
<212> TYPE: DNA
<213> ORGANISM: Artificial Sequence
<220> FEATURE:
<223> OTHER INFORMATION: Sense oligonucleotide

<400> SEQUENCE: 12
gcacggcttg aacaaacacc                                                 20

<210> SEQ ID NO 13
<211> LENGTH: 20
<212> TYPE: DNA
<213> ORGANISM: Artificial Sequence
<220> FEATURE:
<223> OTHER INFORMATION: Sense oligonucleotide

<400> SEQUENCE: 13 caacggpttg aacaaacacc                                                 20

<210> SEQ ID NO 14
<211> LENGTH: 20
<212> TYPE: DNA
<213> ORGANISM: Artificial Sequence
<220> FEATURE:
<223> OTHER INFORMATION: Sense oligonucleotide

<400> SEQUENCE: 14
acaagggtag accaaacacc                                                 20

<210> SEQ ID NO 15

```
<211> LENGTH: 20
<212> TYPE: DNA
<213> ORGANISM: Artificial Sequence
<220> FEATURE:
<223> OTHER INFORMATION: Sense oligonucleotide

<400> SEQUENCE: 15
gcaagggtgg accaaacacc                                                      20

<210> SEQ ID NO 16
<211> LENGTH: 20
<212> TYPE: DNA
<213> ORGANISM: Artificial Sequence
<220> FEATURE:
<223> OTHER INFORMATION: Sense oligonucleotide

<400> SEQUENCE: 16
gcattgacgg accaaacacc                                                      20
```

V_HNAR ANTI-CYTOKINE DOMAINS

CROSS-REFERENCE TO RELATED APPLICATIONS

This application is a continuation of U.S. application Ser. No. 12/939,195, filed on Nov. 4, 2010 and granted on Jul. 30, 2013 as U.S. Pat. No. 8,496,933, which claims the benefit of U.S. Provisional Application No. 61/258,118, filed on Nov. 4, 2009, both of which are hereby incorporated by reference in their entireties.

REFERENCE TO SEQUENCE LISTING SUBMITTED ELECTRONICALLY

The content of the sequence listing text file (File Name: SequenceListing.txt; Size: 10,238 bytes; and Date of Creation: Jul. 15, 2013) filed herewith with the application is incorporated herein by reference in its entirety.

BACKGROUND OF THE INVENTION

Field of the Invention

The present invention concerns therapeutic compositions containing proteins that are the variable regions of IgNAR immunoglobulins, denominated vNAR and codified by sequences denominated $V_H$NAR, that specifically bind and neutralizes cytokines involved in a diversity of process such as inflammation and neovascularization.

SUMMARY OF THE INVENTION

The present invention refers to isolated amino acid sequences originated from elasmobranchi immunoglobulins type IgNAR (Immunoglobulin New Antigen Receptors), including their codificant nucleotide sequences; these amino acid sequences are the variable regions denominated vNARS, (codified in the correspondent $V_H$NAR genes), and refers to use of these molecules for topic treatment of diseases, depending of their specificity. Particularly, the invention refers to vNARs with specificity to bind and neutralize cytokines, particularly interleukines 1 and Tumor Necrosis Factor alpha (TNF-alpha) and Vascular Endothelial Growth Factor (VEGF). In general, the invention refers to the ability of these molecules to reach immunoprivileged organs such as central nervous system, the anterior chamber of the eye, inner ear, or testis; the invention also refers to ability of vNARS to treat solid tumor angiogenesis.

RELATED ART

Antibodies are important tools for medical applications. Most antibodies are composed of two heavy and two light chains, both chains form the antigen binding site. Non conventional antibody structures have been found in llamas, camels, and cartilaginous fishes, these antibodies consist of a single heavy chain with four constant domains and an antigen binding site or variable domain denominated $V_H$H, hcAbs in camels and vNAR or $V_H$NAR in elasmobranches, and are able to bind a broad range of proteins, haptens and peptides.[1]

In a more precise way, present invention refers to isolated proteins whose sequences were selected from variable regions denominated vNAR from IgNARs antigen receptor immunoglobulins from elasmobranches with specificity for cytokines. It also refers to pharmaceutical compositions containing these vNAR, to be used in the treatment of diseases caused by cytokines through inhibition of cytokine activities, in particular for inhibit the activity interleukin-1 (IL-1) and IL-6, Tumour Necrosis Factor (TNF) and Vascular Endothelial Growth Factor (VEGF), the IgNARs derived vNARs are designed for topic or systemic treatment of inflammatory diseases, and to inhibit angiogenesis, for example in the treatment of tumours or in the age-related macular degeneration (AMD).

The $V_H$NARs and vNARs of this investigation have their origin in the shark species *Heterodontus francisci*, they have been isolated and characterized by their affinity to certain cytokines and their capabilities to neutralize the functions of such cytokines, these antibodies are denominated IgNARs and are generated by the immunological system of cartilaginous fishes like sharks, mantas, rays and chimeras.

Antibody technology has been developed to provide new therapies and diagnostic systems, it includes for example the use of monoclonal antibodies, of humanized antibodies designed to decrease the non-human antigen response and conjugated antibodies to improve their properties. The number of antibodies approved by FDA for the treatment of several human diseases has been increasing, approximately 352 of them are on clinical trials (phase I and phase II), accounting for around 25% of all the proteins on clinical trials. A lot of effort has been done in order to reduce the conventional size of antibodies and preserving their antigen binding properties like affinity, avidity and specificity.[2]

Small fragments of antibodies with antigen binding ability are among the technologic alternatives for medical use, such alternatives have progressed from recombinant molecules like the fragment of antigen binding (Fab) and the single chain variable fragment (scFv) to single binding domains for proteins based on immunoglobulins with $V_H$ domains, which in turn have been used to develop new immunotherapeutic and immunodiagnostic strategies. Mimetics of the Fab's to smaller domains is advantageous since that increases the stability and the possibility for accessing antigenic epitopes that are not recognized by conventional antibodies.[2]

There are three isotypes of immunoglobulins or antibodies from cartilaginous fishes, two of them with two standard heavy and light chains, designated as IgM and IgW (also called IgX or IgNARC) and one atypical isotope called IgNAR which is a homodimer of heavy chains not associated with light chains. The shark antigen receptor immunoglobulins (referred as IgNAR or NAR) have a single variable domain (sdAb fragments) and two fork hypervariable structures to include the entire repertoire with union specificity to recognize the antigens. IgNARs are high soluble and high thermostable small molecules (12 kDa) which makes IgNARs a good resource for antibody engineering and therapeutic antibodies.[3]

The present invention concerns to selection and isolation of IgNAR antibodies, in particular of its variable region vNAR, originated in the immunized shark *Heterodontus francisci* with affinity for cytokines and ability to neutralize the activities of such cytokines, these antibodies are originated generally by the immunological system of cartilaginous fish (sharks, skates, rays, and chimeras). The molecular arrangement of the IgNAR antibodies consists of five constant regions and one variable region which in addition is very similar to the $V_H$H found in camelids, which possibly represents an evolutionary convergence at molecular level, and are able to bind a wide range of proteins, haptens and peptides.[1,4]

Nuttall and collaborators obtained a shark non immune antibody library, through phage display technology based on variable regions of IgNAR of the shark *Orectolobus macula-* tus. These regions have the ability to recognize proteins like gingipain protease K from *Porphyromonas gingivalis*, the mitochondrial import receptor Tom70, the lysozyme and the Apical Membrane Antigen 1 (AMA1) of *Plasmodium falciparum*, among others. These regions have been cloned in *Escherichia coli* expression system, being the first description of antigenic specificity of NARs obtained from the natural repertoire of the shark as a probable source of high affinity single domain antibodies.[5,6,7]

Dooley and collaborators in 2003 selected a library generated in *Ginglymostoma cirratum* which was immunized with hen egg lysozyme (HEL), resulting in highly specific clones to HEL antigen, with a nanomolar affinity (ranging from $10^{-7}$ to $10^{-10}$ M) and with a great resistance to heat denaturalization, since they conserved more than 20% of its activity after 3 hrs of incubation at 100° C.[8]

The genes of IgNAR are grouped; each group consist of a single variable simple region (VH), three elements of diversity (D) and a single joining gene (J). The primary repertoire of IgNAR VH is generated by four recombination events, resulting in a diverse repertoire of CDR3 both in terms of sequence and length.[5]

The sequence AGC/T is a mutation "hot spot" of mutations by substitution of bases, differing from that mechanism present in mammals where the mutations occur in regions with pairs of GC. Also, many mutations occur in pairs or triplets, presumably to conserve the reading frame.[3]

Different technologies with shark proteins reactive to antigens were developed immediately after the discovery of these single chain antigen receptors due to their high functionality; its variable domain is 20% smaller than the domain of camelid antibodies. The isolated and cloned variable domain is very stable; it posses the same antigen binding ability than the original receptor. The advantage of this technology is that it combines the properties of the conventional antibodies with the advantages of the small molecules when used as drugs, they have high specificity and low inherent toxicity, because of their low molecular weight they have more possibilities to reach their target site, they are capable of inhibiting enzymes and they can reach also the binding site of cell receptors, this property can be exploited for therapeutic uses. They have a great potential for being administrated by diverse routes and also can be used as topic drugs. Finally, their production is easy and at low cost.[4]

According to Riechmann and Muyldermans (1999), when they compared $V_HH$ camel antibodies with the human $V_H$ fraction, it could be possible to design human modified (chimerical) $V_H$ fragments with the features of being small and efficient units of recognition and therefore, they could compete successfully with the scFv in diverse applications.[8] Therefore, the use of $V_HNAR$ isolated antibodies can compete with both scFv and chimerical antibodies.[4]

DETAILED DESCRIPTION OF THE INVENTION

The present invention relates to immunotherapies and development of pharmaceutical compositions containing effective amounts of protein corresponding to immunoglobulin variable regions called vNAR, and codified by their sequences called $V_HNAR$, for topic uses, the main objective of this invention refer to immunotherapies using these vNARS to reach target tissues or target organs that are of difficult access for IgM or IgG immunoglobulins.

The main objective of the invention refers to isolated proteins vNAR characterized for the ability of reach, bind, and neutralize the activity of one antigenic molecule localized in an immunoprivileged organ such as central nervous system, the anterior chamber of the eye, inner ear, or testis.

The present invention relates to immunotherapies and development of pharmaceutical compositions containing effective amounts of protein corresponding to immunoglobulin variable regions called vNAR, and codified by their sequences called $V_HNAR$, for use in inflammatory responses dependent on the action of proinflammatory cytokines, specifically tumor necrosis factor (TNF), Factor-Vascular Endothelial Growth (VEGF) and interleukins 1, 6 and 8 (IL-1, IL-6, IL-8).

Pro-inflammatory cytokines have a crucial role in sepsis and psoriasis: Sepsis is defined as a systematic inflammatory reaction resulting from an infection.

The clinical symptoms results from interaction between infectious agents with the endogenous defense systems causing both a local and a systematic liberation of a series of mediators with interrelated complex actions. The cytokines, the acute phase proteins and other proteins resulting from biological cascades, as the complement system, the arachidonic acid, free radicals and coagulation factors, act as mediators that initiate their action through the infection stimuli in order to eliminate the infectious agent.[9]

Sepsis can be classified from moderate to very dangerous (septic shock and multiple organ dysfunction syndrome (MODS) previously known as multiple organ failure (MOF)). Sepsis at present constitutes the first cause of mortality in the units of intensive therapy, accounting for more than 60% of the deaths.[10]

Sepsis is clinically characterized by the presence of two or more of the following variables: Hyperthermia (>38° C.) or hypothermia (<36° C.), Tachycardia (>90 palpitations/min), Tachypnea (>20/min or pCO2<32 mmHg), Leucocytosis or leukopenia (>12.000 or <4.000 cells/mL).[9]

Severe sepsis is accompanied by signs of organic dysfunction or organic perfusion disturbance: Lactoacidosis>2.5 mmol/l, oliguria<30 ml/h, acute mental alteration or hypotension (RR syst<90 mmHg or decrement in RR syst>40 mmHg. Severe sepsis accompanied by low blood pressure, in spite of an optimal volume resuscitation and after the exclusion of other causes of hypotension, is called septic shock.

The Tumour Necrosis Factor alpha (TNF-α), is a cytokine released by the macrophages during a local infectious process, for example in response against bacteria or bacterial endotoxins. The effects of vasodilatation, endothelial thinning, vascular occlusion increased by excessive coagulation, activation of leukocytes and chemotaxis, all above promote local arise of a bactericidal microenvironment, with the subsequent draining of the infection through the lymphatic system; also, the processes of antigen presentation and activation of the adaptive immune response are present; nevertheless, in a systemic infectious process caused by bacteria, as occurs in sepsis, released TNF-α by the activated macrophages produces the same effects: vasodilatation, endothelial thinning, vascular occlusion increased by excessive coagulation, activation of leukocytes and chemotaxis, however, as these effects are not locally promote a peripheral ischemia, organic failure, disseminated intravascular coagulation (DIC) and sepsis with their signs: systemic hypotension, edema, hypovolemia, neutropenia and fever. In addition to TNFα, activated macrophages release interleukines 1, 6, 8 and 10, gamma interferon, arachidonic acid derivatives, oxygen radicals and proteases. All above influence the appearing of organic dysfunction.[11, 12, 13]

The therapeutic focus for sepsis includes the eradication of the pathogen, the metabolic and haemodynamic stabilization, the modulation of the inflammatory response (high levels of cytokines are related to a greater multiple organ failure) and of the coagulation.[9]

One of the objectives of the present invention is the selection and production of anti-TNF-alpha VHNARs molecules designed for the treatment of sepsis events through diverse administration routes with therapeutically effective doses.

Regarding to psoriasis, this is a chronic erythematosquamous inflammatory disease of the skin, which affects 1% to 3% of the worldwide population, and also psoriasis is responsible for a significant increase of the biopsychosocial morbidity in those patients suffering it. Psoriasis is a multifactorial disease; it can be eruptive-like, erythrodermic, nail psoriasis, scalp psoriasis or the called psorisis vulgaris that affects 80% to 90% of patients with psoriasis, it appears as inflamed areas on the skin called hyperkeratotic and prurigenous plaques which a come out in any place but more commonly in the scalp, elbows, knees and trunk. In general, any type of psoriasis is characterized by excessive but controlled keratinocyte proliferation, and abnormal differentiation of that cells and skin infiltration by inflammatory cells; hyperproliferation is caused by persistent T cell stimulation by immunogens of epidermal origin.[14]

Contributing factors for psoriasis include the combination of genetic, environmental and immunological factors, in people with predisposition, superantigens like bacteria, virus and fungi, vaccinations, intramuscular injections, certain medications, stress, and wounds in the skin could trigger the psoriasis.[14]

The primary activity of the psoriasis takes place in epidermis, but the problem is originated in the basal layer of the skin where the keratinocytes go toward the epidermis in an abnormal accelerated way so the skin cannot eliminate them at a normal rate therefore thick and dry plaques arise on skin, the histological alterations include skin edema, dilation of papillar vessels in dermis and perivascular cell infiltration by T cells, dendritic cells or monocytes/macrophages, with a subsequent infiltration of CD8+ T cells and also granulocytes that particularly are found in the epidermis. Microabcesses are formed and the superficial skin dies; dermis that contains nerves, blood and lymphatic vessels that nourish keratinocytes which multiply in an abnormal rate and becomes the skin red and inflamed.[15]

Psoriasis should be treated as a chronic inflammatory condition, that appears because of the persistent stimulation of the T cells by immunogens of epidermal origin that initiated by the activation of the T cell that migrated to the skin. In more detail, the type of cytokines released by Th1-type T cells are responsible for the inflammatory response in the psoriasis, are TNF, IFNγ, IL-6, 8 and 12. It has been observed that TNF increases the synthesis of IL-1, IL-6 and IL-8; also activates the nuclear transcription factor (NF-κB) and increases the hepatic synthesis of acute phase proteins, thus contributing to the constitutive symptoms, becoming a severe psoriasis. TNFα, induces maturation of Langerhans cells, making these cells more efficient to present antigens to T cells, and promoting their migration from skin to lymph node, due to a decreased expression of E-cadherin (molecules that help bind together the Langerhans cells to keratinocytes). In addition, the expression of the vascular endothelial growth increases, leading to neovascularization and migration of leukocytes to the skin. TNFα increases the plasminogen activator inhibitor type 2, which protects cells from apoptosis, leading to increased longevity of keratinocytes, and thus a thickening of the epidermis.[14]

The initiation of TNF-mediated events involve the attachment of homotrimers of TNF to cell surface receptors, changing the molecular conformation of the receptors and signal transduction through the intracellular domain of the receptor. It has been shown that naturally occurring soluble forms of TNFα receptors are able to act as competitive inhibitors for binding TNFα to cell surface receptors. However, the presence of these natural antagonists is not sufficient to block the activity of elevated levels of TNFα observed in the most of inflammatory diseases.[15] Since 1995, clinical trials have been conducted using different TNF inhibitors, these were monoclonal antibodies, humanized, chimeric antibody fragments, soluble receptor p55, and the expected response in reducing mortality or increasing survival has been presented in these studies of inconsistent data, so further investigation has been required.[13, 14]

25% of patients with severe psoriasis require phototherapy and/or a systematic treatment. In long-term, the treatment could complicate because of limitations related to the drugs therefore, for the management of psoriasis, the incursion of new biological therapies based on proteins are necessary in order to expand and improve the therapeutic possibilities.

Sepsis, psoriasis and other diseases are likely to be controlled by immune therapy for efficacy and safety. Drugs inhibitors of TNF pathway that have been studied include antibodies created by bioengineering (Infliximab, Etanercept and Adalimumab) and therapies directed against T cells (Efalizumab and alefacept). These antibodies are new to dermatology, these concepts and some of these drugs have been used in rheumatology. The original safety profiles of these drugs were first discussed in the literature of that specialty. Currently, those beginnings have been supplemented with psoriasis patient populations with different risk profiles relative to patients affected by rheumatoid arthritis.[13, 14]

Etanercept is indicated for improving physical function in patients with psoriatic arthritis. It inhibits TNF activity by competitive binding to this cytokine and preventing interaction with its cell surface receptor. The dimeric nature of Etanercept allows protein binding to two TNF molecules attached to a receiver or free, with an affinity of 50 to 1000 times the monomeric forms of soluble TNF receptor.[15, 16]

TNF found in psoriatic lesions, can stimulate cytokine production and expression of adhesion molecules by keratinocytes and vascular endothelial cells, these signals cause the recruitment of additional inflammatory cells into the plaque, so it was considered that TNF acts by amplifying and sustaining the inflammatory process characteristic of psoriasis. Biological agents introduced for the treatment of psoriasis showed no evidence of toxicity in the bone marrow, liver and kidney. So far, their use has been approved by the FDA in the Etanercept Psoriasis, Alefacept Efalizumab and psoriatic arthritis and etanercept. Other therapies are in Phase III investigation. The Etanercept, Efalizumab and infliximab are associated with early clinical response within four weeks of therapy.[16]

In the state of the art, new findings about the role of various types of immune system cells such as dendritic, h17, gamma-delta T cells, NK cells and regulatory T, have reported the effects of activation of signal transduction in keratinocytes and the role of mediators such as IL-22, IL-23 and IL-20. With all this, coupled with successful use that the state of the art reported on anti-TNF therapy in psoriatic patients, it is possible to raise the use of combination therapies, including personalized therapies.[14]

Concerning the use of TNF-alpha antagonists to treat sepsis, it is an immunomodulatory strategy requiring appropriate implementation in time and dose to be successful, and must come together to combat the causative agent using appropriate antibiotics, elimination of septic foci, cardiovascular hemodynamic monitoring, fluid and electrolyte therapy, use of ionotropes and vasoactive control of blood oxygenation and ventilation and adequate nutritional intake.[16, 17]

Within the scope of the present invention includes the use of combination therapies which are considered, provided they are safe for the patient. It is included in the scope of the invention, the use of shark antibodies specific for TNFα combined with the use of: antibiotics, immunosuppressive drugs like cyclosporine or cytostatics such as methotrexate, in combination with antibodies anti-endotoxins, antioxidant compounds, nitric oxide antagonists, antagonists of IL-1, antibodies antiCD-14, protein kinase inhibitors, blocking NF-Kappa gene-beta, cyclooxygenase inhibitors, anticoagulant therapy, inhibitors of cell adhesion molecules, the combination with keratolytic treatments, emollients, vitamin D analogues or vitamin A, and combination treatments of herbal origin.

An object of the present invention relates to the use of alternative therapeutic recombinant antibodies specific shark used to block TNF locally in the affected skin, therefore having less side effects of systemic use themselves, also proving the better adherence to treatment compared with parenteral application, in addition to being smaller molecular antibodies that antibodies and fusion proteins with similar functionality described in the prior art, there is an improved bioavailability, which reduces the dose therapeutically effective with respect to the doses used in therapy with other systemic or subcutaneous anti-TNF agents.

Role of proinflammatory cytokines in Rheumatoid Arthritis: Rheumatoid arthritis has a prevalence of about 1%, with a wide spectrum of severity and age in the effects to the joints, can become a disabling disease.[18]

Cytokines derived from macrophages and fibroblasts that are abundantly present and speaking at length, in synovial fluid, including IL-1, TNF, colony stimulating factor and granulocyte macrophage-GM-CSF, IL-6 and many chemokines such as IL-8, all influence the inflamed and infiltrated state of lymphocytic of the joints, and eventual degeneration of cartilage and bone. Despite the presence of anti-inflammatory cytokines establishing homeostasis is not achieved. The cytokine TNF is considered more important to regulate the process and so is the therapeutic target. Clinical studies have demonstrated the success of therapy with anti-TNF or against its receptor.[18]

Another object of this invention is the use of therapeutic alternative recombinant shark antibodies and its specific $V_H$NAR regions to block TNF used locally or systemically to treat rheumatoid arthritis, it is important that local or topical use will diminish side effects of systemic use, and a better adherence to treatment compared with parenteral application is also evident.

An specific objective of the present invention refers to the inhibition of angiogenesis or neovascularization, that is, the growth of new blood vessels, including to their therapeutic uses by neutralizing VEGF activity with the vNARs herein defined, angiogenesis is a "common denominator" shared by diseases affecting more than one billion people worldwide. This includes all cancers, tumor angiogenesis, cardiovascular disease, blindness, arthritis, complications of AIDS, diabetes, Alzheimer's disease, rheumatoid arthritis, psoriasis, atherosclerosis, amyloid lateral sclerosis, age-related macular degeneration (AMD), diabetic retinopathy, sepsis, vascular glaucoma, corneal angiogenesis, and other major health conditions. This objective is achieved with the isolated and here defined vNAR that is specific for VEGF, then neutralizing its angiogenic function.[19]

The vascular endothelial growth factor (VEGF) was described as a tumor-derived factor with the ability to induce endothelial cell permeability, cell proliferation and angiogenesis. VEGF is involved in pathological processes.

In cancer tissue, the elevated levels of VEGF are associated with an increased metastatic ability of tumour cells through increased angiogenesis and stimulation of the development of the lymphatic system; besides induction of cell proliferation and migration, VEGF may also play a role in cell survival through autocrine functions. Tumour cells secrete VEGF under stressed conditions as hypoxia, radiotherapy and chemotherapy. These elevated levels of VEGF in tumour tissue are associated with a poor response to treatment and thus poor prognosis.[20]

In case of proliferative diabetic retinopathy, that is a major complication of diabetes, is characterized by the growth of new blood vessels from the pre-existing retinal circulation into the vitreous humour, i.e., it is a process of angiogenesis. The initial insult is capillary loss in the mid-peripheral and peripheral retina. The resultant retinal hypoxia stimulates the production of pro-angiogenic growth factors, with VEGF and the growth hormone/insulin-like growth hormone-1 axis being implicated in the resultant angiogenic response. The ischaemic retina is unable to support revascularization for reasons that are poorly understood. Instead the collagen fibrillar network of the vitreous humour supports a process of angiogenesis and new blood vessels grow into the vitreous cavity (periretinal neovascularization). As well as providing a mechanical support for growth, collagen fibrils provide critical signaling for angiogenesis through integrins, including $\alpha2\beta1$ integrin, on endothelial cell surfaces. Visual loss is caused by the new blood vessels in the vitreous humour bleeding, and by the contraction of scar tissue associated with these blood vessels leading to tractional retinal detachment.[21]

From the literature it is clear that overexpression of VEGFs and their receptors VEGFR-1, VEGFR-2 and VEGFR-3 is causing increased microvascular permeability and angiogenesis in eye conditions such as diabetic retinopathy and also in AMD. The cellular distribution of VEGFR-1, VEGFR-2 and VEGFR-3 suggests various specific functions of the VEGF family in normal retina, both in the retinal vasculature and in neuronal elements.[22]

Different strategies have been developed to inhibit VEGF-mediated signaling, however, since it showed that a specific anti-VEGF antibody could inhibit tumor growth in animal models described by Ferrara, Davis-Smith, in 1997 began developing a human version of anti-VEGF antibody.

Bevacizumab is an anti-VEGF monoclonal antibody that is the first antiangiogenic agent approved for cancer treatment; it has been approved for use for first-line treatment of metastatic colorectal cancer in combination with a chemotherapy regimen, it has been tested in cancers of many organs with clinical outcomes including tumor regression and increased medium to long-term survival rate.[19]

In 2004, the FDA accepted the Pegaptanib, the first antiangiogenic drug for the eye, this anti-VEGF was analyzed in studies of patients with age-related macular degeneration, demonstrating stabilization of vision in 70% of treated patients, versus 50% in patients not treated with this antibody. In 2006, the FDA approved the use of ophthalmic Ranibizumab, which is a recombinant Fab fragment of humanized murine monoclonal antibody anti-VEGF, they have also been used successfully in the treatment of eye diseases for the inhibition of neovascularization that leads to blindness, especially for treating macular degeneration in all its forms, including wet AMD, the most common type.[20]

The development of new treatments is required in order to inhibit the VEGF activity vinculated to pathophysiologies, so that the medication needed for the therapy, because of its intrinsic activity or by its method of administration (topic), will be more efficient and involve less side effects such as hypertension, proteinuria, bleeding, damage to the healing of surgical wounds, even fatal complications such as arterial thrombosis, focal gastrointestinal perforation and reversible posterior leukoencephalopathy.[19]

The aim of the present invention is to provide vNAR molecules derived from shark antibodies, specifically the Horn shark species capable of neutralizing VEGF activity for use in treating pathophysiologies which involves the phenomenon of neovascularization, the treatments can be directed to conditions such as: Retinal Neovascularization, Choroidal Neovascularization, Corneal Neovascularization, Macular Degeneration, Retinal Diseases, Diabetic Retinopathy, vitreous hemorrhage, retinal hemorrhage, choroiditis, retinal detachment, Drusen retinal neovascular glaucoma, Choroid Diseases, Uveitis, Eye Infections, Occlusion Retinal Artery, Myopia Degenerative, Occlusion Retinal Vein, Chorioretinitis, Histoplasmosis, Uveal Diseases, Epiretinal Membrane, Coloboma, Neoplasms choroid, retinal degeneration, retinitis, Retinal Perforations, Retinopathy of Prematurity, cystoid macular edema, papilledema, Optic Disk Drusen, angioid streaks, Retinitis Pigmentosa, Vision Disorders, sympathetic ophthalmia, Scar, Burn Ocular Recurrence Ischemia Eye Injuries Glaucoma, Eye Hemorrhage, Scotoma, posterior uveitis, Fungemia, Retinal Neoplasms, opacity of the cornea, anterior uveitis, hyphema, Sarcoidosis, Retinal Vasculitis, Osteoma, Cytomegalovirus Retinitis, atrophy, Phlebitis, Keratoconus, disorders Substance-Related, Eye Injuries, Penetrating, Diabetes Mellitus Type 2, vitreoretinopathy Proliferative, Bleeding, Diabetes Mellitus Type 1, Optic Nerve Diseases, Vascular Diseases.

Another object of the invention is the use and production of shark antibodies derived from $V_H$NAR, specifically from the Horn shark species because of its high ability to neutralize VEGF activity in order treat pathophysiologies involving the phenomenon of neovascularization, treatments can be used for various conditions such as tumor initiation and tumor progression. The vNAR neutralizators of the VEGF activity are evaluated in animal models especially using animal models of solid tumors, orthotopic tumor models, tumor xenotransplantation models, genetically engineered mouse models (called GEMs of genetically engineered models). The anti-VEGF vNARs described herein can be used alone or in combination with other drugs or treatments in order to eliminate solid tumors that develop in liver, lung, brain, breast, prostate, colon or kidney.[20]

More particularly, the invention is directed to the treatment of inflammatory responses through the use of antibodies as therapeutic vNAR agents that act as antagonists of these cytokines, these vNAR have the particularity of having a better tissue penetration unlike the antibodies used for the same purposes described in the prior art, they also have low immunogenicity, and better excretion, besides being a technology with cost-benefit advantages.

Antagonists of the invention are particularly directed to the treatment of rheumatoid arthritis, acute systemic inflammatory syndrome associated with infection (sepsis) and skin inflammations such as psoriasis.

The present invention consists of several stages beginning with the generation of a gene bank of immunoglobulin IgNARs of the Horn shark, and the selection of vNAR clones with specificity for human cytokine particularly to TNF-α and VEGF, and its expression through the technique of phage display.

A peculiarity of the present invention refers to the collection and use of shark antibodies TNF- and others with specificity for VEGF, which were obtained by extracting RNA form the Horn shark previously subjected to a rigorous protocol immunization with either human TNF or by human VEGF.

From the shark antibodies were obtained two antibodies named clone 43 and clone 65 with specificity for TNFα, the obtained amino acid sequence for this $V_H$NARs were obtained following the phage display technique.

The clone 43 was characterized by having high specificity for human TNFα its amino acid sequence is identified in the list of sequences as SEQ ID NO:1 and is the next one:

```
ASLDQTLRTATRETGESLTVNCVLVDAIYGLYSTSWYRNNPGSTDREHIT

IGGRYVESVNKGAKSFSLQIKDMTFEDSGTYYCKARATSGYTPHDGSGTV

LTVN
```

Some specific homologues are also defined for the protein having the amino acid sequence SEQ ID NO:1, as follows: the amino acid residue 28 is one of Ile or Asn, the amino acid residue 33 is one of Ser or Asn, the amino acid residue 75 is one of Phe or Val, the amino acid residue 88 is one of Thr, Ala or Glu, the amino acid residue 89 is one of Ser or Thr, the amino acid residue 90 is one of Gly, Asp or Ser, the amino acid residue 91 is one of Tyr or Gly.

The DNA sequence that codifies for the protein of clone 43 specific for TNFα is the following one (identified as SEQ ID NO:2 in the list of sequences):

```
gcaagcctgg accaaacact aagaacggca acgagagaaa caggcgaatc cctgaccgtt      60
aactgcgtcc tcgttgatgc tatctatggt ttgtacagca catcttggta ccgcaataat     120
ccgggttcaa cagacaggga acacataacg attggcggac gatatgttga atcagtcaac     180
aaaggagcaa agtcattttc tctgcaaatc aaggacatga catttgaaga cagtggcacc     240
tattactgca aagcgcgagc tacatctggg tataccccccc acgacggatc tggcaccgtg     300
ctgactgtga ac                                                         312
```

The clone 65 was characterized by having also high specificity for human TNFα its amino acid sequence is identified in the list of sequences as SEQ ID NO:3 and is the following one:

```
ASLDQTPRTATRETGESLTVNCVLVDANYGLYNTSWYRNNPGSTD

REHITIGGRYVESVNKGAKSFSLQIKDMTVEDSGTYYCKARESDYNR

VGIRDYKDYDGAGTVLTVN
```

The DNA sequence that codifies for the protein of clone 65 specific for TNFα is the following one (identified as SEQ ID NO:4 in the list of sequences):

```
gcaagcctgg accaaacacc aagaacggca acgagagaga caggcgaatc cctgaccgtt      60
aactgcgtcc tcgttgatgc taactatggt ttgtacaaca catcttggta ccgcaataat     120
ccgggttcaa cagacaggga acacataacg attggcggac gatatgttga atcagtcaac     180
aaaggagcaa agtcattttc tctgcaaatc aaggacatga cagttgaaga cagtggcacc     240
tattactgca aagcgcgaga gagcgactac aatagggtag gtatacggga ctacaaggac     300
tacgacggag ctggcaccgt gctgactgtg aacgg                                335
```

The alignment shown in FIG. 1, belongs to the sequences that resulted reactives for the cytokine TNFα these are the clones also named TNF43 and TNF65.

The clone 13 resultant have high specificity for human VEGF, its amino acid sequence is the next one (identified as SEQ ID NO:5 in the list of sequences):

ASLDQTPRTA TRETGESLSI NCVLTDTSHI LFGTKWLWNN

PGSTDWESIT IGGRYAESVN NQAKSFSLQI KDLTVEDSGT

YYCKAQTIGR RKNLLPRPLV NGIAAMGYSS SDYDGAGTVL TVN

The DNA sequence that codifies for the protein of clone 13 specific for VEGF is the next one (identified as SEQ ID NO:6 in the list of sequences):

gcaagcctgg accaaacacc aagaacggca acgagagaga caggcgaatc cctgagcatt 60
aactgcgtcc tcactgatac tagccatatt ttgttcggca caaaatggct ctggaataat 120
ccgggttcaa cagattggga aagcataacg attggcggac gatatgctga atcagtcaac 180
aaccaagcaa agtcattttc tctgcaaatc aaggacctga cagttgaaga cagtggcacc 240
tattactgca aagcgcaaac cataggaaga cgcaaaaatc tacttccacg cccattggtg 300
aacggtatag ctgcgatggg gtatagctcc agtgactacg acggagctgg caccgtgctg 330
actgtgaac 349

The clone 43 resultant of expression in *P. pastoris* have the next amino acid sequence (identified as SEQ ID NO:7 in the list of sequences):

ASLDQTLRTATRETGESLTVNCVLVDANYGLYSTSWYRNNPGSTDREHIT

IGGRYVESVNKGAKSFSLQIKDMTVEDSGTYYCKARATSGYTPHDGAGTV

LTVNSLEQKLISEEDLNSAVDHHHHHH*

The DNA sequence that codifies for the protein of clone 43 specific for TNFα is the next one (identified as SEQ ID NO:8 in the list of sequences):

GCAAGCCTGGACCAAACACTAAGAACGGCAACGAGAGAGACAGGCGAATC

CCTGACCGTTAACTGCGTCCTCGTTGATGCTAACTATGGTTTGTACAGCA

CATCTTGGTACCGCAATAATCCGGGTTCAACAGACAGGGAACACATAACG

ATTGGCGGACGATATGTTGAATCAGTCAACAAAGGAGCAAAGTCATTTTC

TCTGCAAATCAAGGACATGACAGTTGAAGACAGTGGCACCTATTACTGCA

AAGCGCGAGCTACATCTGGGTATACCCCCCACGACGGAGCTGGCACCGTG

CTGACTGTGAACTCTCTAGAACAAAAACTCATCTCAGAAGAGGATCTGAA

TAGCGCCGTCGACCATCATCATCATCATCATTGA

Besides the generation of a Gene Bank of IgNAR immunoglobulins from *Heterodontus francisci*, and the selection of $V_H$NAR clone specific for VEGF and TNFα, and their expression, the present invention refers to formulation of stable pharmaceutical compositions that contains the correspondent vNARs such as topical formulations suitable to be administered in skin and mucosa or for ophthalmic administration in injectable solution or in topical drops, other alternatives include those techniques to release the active proteins in the target organ of the patient.

The pharmaceutical compositions containing vNARs anti-TNFα or anti-VEGF could be specially developed as topical preparations for epithelium, without loss of neutralizing ability for at least two years, these compositions comprises pharmaceutically acceptable vehicles that can be, but are not limited to, the following ones: neutral base cream, gel, jelly, ointment, spray, patches or powders, or combinations thereof. The cream base contains an emulsifying agent, an ingredient in oil phase and water phase ingredient. The emulsifying agent may be polyoxyethylene fatty alcohol ether (Peregal A-20), polioxystearate (SG-6), or a combination of these. The oil phase ingredient can be, but not limited to: cetyl alcohol, stearyl alcohol, stearic alcohol, liquid paraffin, and dimethicone. The aqueous agent phase may be glycerol and ethyl paraben. Preferably, the antibodies present in topical preparations are not more than approximately 100 to 50 micrograms per gram of cream base. The topical preparations can be applied once a day in an effective dose that can be of approximately 0.1 to 10 micro grams of antibody per square centimeter of inflamed skin area.

The invention also refers to pharmaceutical compositions containing vNARS preparations made to be adequate for parenteral administration red to a patient, preferably a human. The pharmaceutical compositions may be suitable to be administered through a continuous infusion for a prolonged-release implant, in an injectable solution, or by any other parenteral administration technique. These compositions contain at vNAR purified and combined with carriers, excipients or diluents physiologically acceptable salt, they may contain buffers, antioxidants, carbohydrates, chelating agents and stabilizers, they can even be combined with other active agents such as antibiotics or IL-1 receptor or IL-2 that are considered preferential use in the treatment of clinical indications specially those associated with the activities of TNFα or VEGF.

The ophthalmic solutions could contain HCl histidine, tetralose-alpha dihydrate, polysorbate 20. The amounts and frequency of administrations depend on the stage and severity of sepsis or septic shock in the patient.

BRIEF DESCRIPTION OF FIGURES

FIG. 1: Alignment of amino acid sequences of clones 43 and 65.

Figure 2:
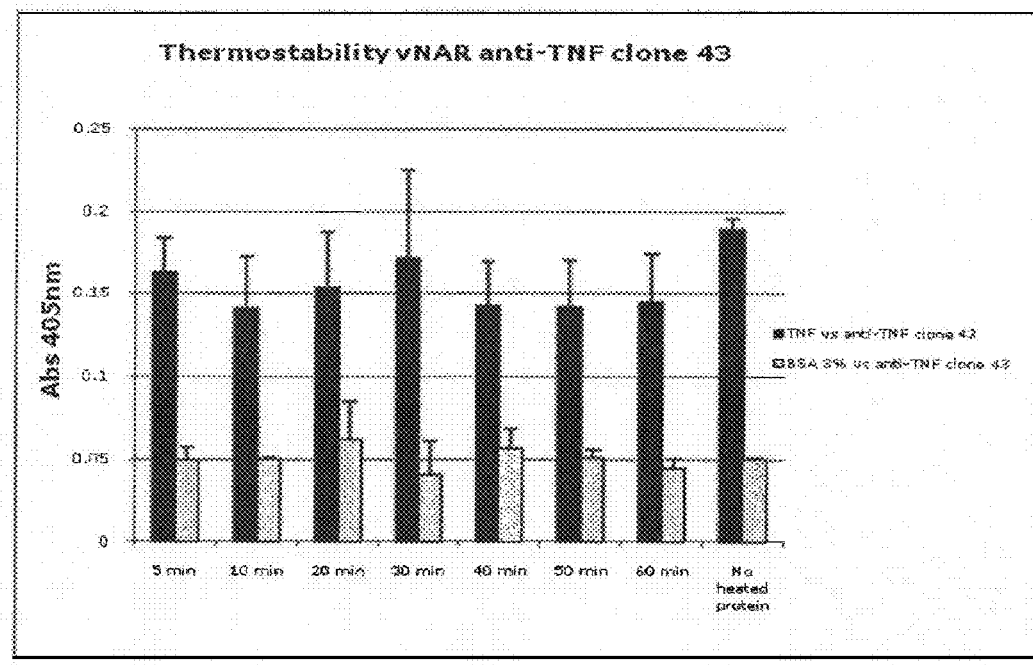
FIG. 2: ELISA result to evaluate the thermostability of clone TNF43 5 µg/ml 50 µl, 90° C. 60 minutes, the results of binding were obtained for each of the registered aliquots.

The following examples are included as an illustration of the best way to obtain and perform the invention, and are representatives of some of their modalities and do not pretend to limit the scope of the invention.

EXAMPLES

Example 1

Production of vNAR Fragments Specific for TNFα

Shark Immunization:

An specimen of *Heterodontus francisci* was immunized with the recombinant human cytokine TNFα. All the immunizations were performed with 1 µg of protein in PBS intravenously, the protocol during 20 weeks, the challenges were done every 15 days, in the same period, bloods of 1 ml must be obtained from caudal vein every 15 days (before each booster shot). The serum was collected and stored at −20° C.

RNA Extraction:

Seven days after final immunization, RNA from the shark's spleen is obtained by phenolic extraction, the concentration and purity is optically measured in absorbances of 260 nm and 280 nm. Store total RNA at −80° C.

Retrotranscription Reaction:

The retrotranscription is carried on using conventional methods, with the first antisense GTTCACAGTCAGCACG-GTGCCAGCTC (SEQ ID NO:11) and 1 µg of total RNA. The fragment is analyzed in 2% agarose gel. This material is used to amplify the variable genes through PCR.

Amplification Reaction:

The sequences in table 1 are used as sense or anti-sense oligonucleotides. The variable chains were amplified by means of PCR.

TABLE 1

| Oligonucleotides specific for amplification of variable fragments | |
|---|---|
| Sequence | |
| Sense GCACGGCTTGAACAAACACC | (SEQ ID NO: 12) |
| Sense CAACGGGTTGAACAAACACC | (SEQ ID NO: 13) |
| Sense ACAAGGGTAGACCAAACACC | (SEQ ID NO: 14) |
| Sense GCAAGGGTGGACCAAACACC | (SEQ ID NO: 15) |
| Sense GCATTGACGGACCAAACACC | (SEQ ID NO: 16) |
| Anti-sense GTTCACAGTCAGCACGGTGCCAGCTC | (SEQ ID NO: 11) |

Both sense and antisense oligonucleotides have an additional sequence that confers a recognizing site to restriction enzyme Sfi1. The amplified fragments is analyzed in electrophoresis gel at final concentration of 50 ng/µl in and ethidium bromide at a final concentration of 50 ng/µl (30 minutes at 100 Volts). The fragments having a size corresponding to that expected in agreement with the oligonucleotide set utilized, are cut from the gel. After that, the DNA is extracted with an special kit.

Digestion of the purified fragment obtained by PCR: 1.5 µg of the purified fragment is digested corresponding to the genes of VNAR with the restriction enzyme Sfi1 (40 U/4), using 5 U of enzyme per µg of DNA to digest, is incubated (5 hours a 50° C.) and inactivates at 65° C. during 15 minutes and storage of the mix at −80° C.

Preparation of expression vector pCOMb3X: The phagemid cloning vector pCOMb3X is purified and analyzed in 1% agarose gel then quantified by electrophoresis means at 260 nm and then digesting with SfiI. The digestion products are purified in 1% agarose gel, recovering from the restricted vector, a ~3400 pb fragment and a ~1600 pb fragment.

Preparation of electrocompetent cells *E. coli* ER2537 and TOP10F': The electrocompetent cells ER2537 and TOP10F' are grown in LB Agar and incubated at 37° C. during the night. Next day an isolated colony is inoculated in 10 ml of Bovine Serum (SB) preheated at 37° C. following overnight incubation at 37° C. and 250 rpm. At the third day 5 ml of the culture are inoculated in SB (500 ml) and incubated at 37° C. and 300 rpm during 2.5 hr ($DO_{600}$=0.6). The culture is transferred to sterile cool tubes, incubated in ice during 15 minutes and centrifugated at 3000 g and 4° C. during 20 minutes. The pellet is resuspended in 10% cool glycerol incubating in ice during 15 minutes then washed three times by centrifugations using 10%, the final pellet is resuspended and aliquoted in small quantities of 50 to 100 µl in dry ice and ethanol, finally storage at −80° C.

Ligation Reaction:

Optimization of reaction ligations is done testing several times to check optimal conditions of the digested fragments. The enzyme T4 DNA ligase is used to link the insert to the vector in a 1:1 molar reaction, the final volume of the reaction can be of 20 μL, with 5 U of enzyme, following 12 hr incubation at 25° C. then inactivating the ligase enzyme at 65° C. for 15 minutes: Positive and negative controls must be included: digested vectors with and without insert. To verify the ligation performance, 1.5 μl of the product of each ligation, is electroporated in small scale (200 Ohms, 2.5 kV and 4 milliseconds) in 50 μl of electrocompetent $E.\ coli$ ER2537 cells. Immediately the electroporation cell is washed with SOC medium, transferred to 15 ml tubes, cultivating 1 hour at 37° C. and 250 rpm, posteriorly grown in LB agar plates with ampicillin having 1 μl, 10 μl y 100 μl of this culture, incubating over night at 37° C. The ligation efficiency is obtained determining Colony-Forming Units CFU.

Large Scale Ligation:

After determining ligation efficiency and transformation, the large scale ligation is performed mixing pCOMb3X digested (1.3 μg) and the $V_H$NAR fragments (350 ng) in a final volume of 2004 incubating during 12 hrs at 25° C. Posteriorly the DNA previously precipitated is resuspended in a final volume of 15 The ligated product is electroporated in 300 μL of ER2537 electro-competent cell, incubating 1 hour at 37° C. and 250 rpm, with 10 ml of SB media and 3 μl of ampicillin (stock 100 mg/ml). A dilution 1:100 from this culture (10 μl and 100 μl) are cultured in LB agar plates over the night with ampicillin. To obtain a representative size of a library of the repertory of $V_H$NAR must be done several large scale ligations.

Primary Library Amplification:

Following the incubation on the last step, the helper phage VCSM13 ($10^{12}$-$10^{13}$ UFC) is added and 2 hrs after is added kanamycin 70 μg/ml agitating over night. The culture is centrifuged (3000 g 15 minutes 4° C.), the supernatant is recovered and added PEG-8000 (8 g) and NaCl (6 g) incubating 5 minutes at 37° C. agitating to dissolve solids, the incubating in ice 30 minutes. Centrifuging at 15,000 g, 15 minutes at 4° C., discarding supernatant and the pellet is resuspended in PBS-BSA (2 ml, 1%), centrifuging at 15,000 g, 5 minutes. The supernatant obtained is sterilized by filtration (0.22 μm membrane) and storage at 4° C.

Phage selection rounds, amplification and recovery: There were performed 4 rounds of phage selection with TNFα 1 μg in PBS in an ELISA plate, sealed and incubating over night at 4° C., the cytokine is eliminated and blocking with 150 μl of PBS-BSA (3%), sealed and incubated 1 hr at 37° C.; discarding and adding 50 μl of phage-antibodies for each well, sealed and incubated with TBS-Tween 20 (0.05%) 150 μl, for each well using the pipette to agitate. The solution is discarded and the phage-antibodies specific for TNFα are harvested after adding 50 μl per well of TBS-Trypsin [10 mg/ml]. The plate is sealed and incubated during 30 minutes, 37° C. The phage-antibodies are recovered and used to infect a culture of $E.\ coli$ ER2537 (2 ml) electro-compentents ($DO_{600}$=1), during 15 minutes at room temperature. The selected phage-antibodies are amplified using serial dilutions incubating the transformants in SB media with carbencillin and helper phage VCSM13 with kanamycin. The phage-antibodies were recovered from the infected cultures of ER2537 cells by centrifugations using first PEG-8000 4% and NaCl 3%, and PBS_BSA 1% (2 ml) filtering the supernatant with a 0.22 μm membrane, using 50 μl para to be selected according to the TNFα binding. Each preparation was titrated using two dilutions $1\times10^{-6}$ and $1\times10^{-8}$, using 1 μl of each one to infect a culture of ER2537, D.O.=1, 50 μl, spreading in petri boxes with LB+Carbencillin, incubating over night at 37° C. and calculating the CFU.

ELISA for phage-antibodies: An immunoenzymatic assay was performed for each preparation of phage-antibodies or plasmids obtained in the 4 selection rounds as follows: In an ELISA 96 plate, by triplicate, were incubated over night at 4° C., 50 μl of each of the cytokines per well (1 μg/ml in PBS), and 50 μl of BSA 3% used as the antigen for negative controls. The following day the solution was discarded and blocking solution was added (150 μl PBS-BSA 3%), incubating for 1 hour at 37° C. Discarding the solution and adding 55 μl of a dilution 1:3 (plasmids: PBS-milk at 3%) preincubating for 1 hour at room temperature, each preparation on phage-antibodies from each round selection ($R_0$-$R_4$); for negative control the phage-antibodies were added to wells with BSA 3%; incubating the plate 2 hrs at 37° C., washing with PBS-Tween 20 (0.1%). Than adding anti-M13 50 μl conjugated with peroxidase diluted: 1000 with PBS-milk at 5%, incubating 1 hour at 37° C., washing the plate and adding 2,2'-Azinobis (3-ethylbenzthiazoline-6-sulfonic Acid) ABTS 50 μl which is the substrate for peroxidase, incubating in dark at room temperature and determining the absorbance at 405 nm ($A_{405\ nm}$) at the end of 30 minutes.

R4 phages TOP10F' transformation: In order to produce soluble protein (IgNARs) without pIII polypeptide are obtained by electroporating 100 ng of plasmid from selected clones into 50 μL of electrocompetent TOP10F' $E.\ coli$, which allow read-through of the amber codon present in the helper phage gene 3. Transformed cells are plating on LB/carbenicillin plates and incubated overnight at 37° C.

Clone identification Transformed TOP10F': $E.\ coli$ cells harbouring the fragment insert of interest, IgNAR codifying sequence, were checked by colony PCR using specific oligonucleotide primers. PCR products were analyzed by gel electrophoresis and ethidium bromide staining.

Low scale expression: Positive PCR recombinant TOP10F' $E.\ coli$ clones were cultured overnight at 37° C. and 250 rpm in SB medium plus carbencillin (100 μg/mL). After centrifugation at 300 rpm, staying 5 hrs at $OD_{600}$≅0.5-0.6), were induced by adding isopropyl-β-D-thiogalactopyranoside (IPTG) (0.5M), continuing the incubation during 20 hrs at 37° C. After centrifugation the cell pellets were obtained from the culture supernatants by centrifugation, then were used to extract the periplasmic fraction using 400 μl of hypertonic solution and were incubated in ice for 20 minutes, centrifuging at 5,000 rpm 15 minutes, 4° C., storing the supernatant and resuspending the pellet in 400 μl of hypotonic solution of $MgSO_4$ 400 5 mM, incubating for 20 minutes at 4° C., centrifuging at 16,000 g for 15 minutes. This supernatant is joined with the former supernatant and were dialyzed with a membrane 3,000 KDa agitating in 4.5 liters of PBS at 4° C., 2 hours after the PBS is changed and dialysis continue over the night. The next day the dializate is transferred to columns Bio-Rad, No. Cat. 737-1051, charged with agarose Ni-NTA 250 μl previously equilibrated with imidazol 20 mM in PBS solution; the dialized passed 3 times through the column and is washed with 5 ml of washing solution (imidazol 35 mM in PBS), eluting 2 times with 250 μl solution of imidazol 250 mM in PBS; staying for 20 minutes each time. The eluted is dialyzed in the mentioned conditions and then collected.

Expression ELISA. 50 μl of the obtained periplasmic fraction that contains the $V_H$NAR, is incubated for 2 hours at 37° C., diluting them 1:1 with BSA 1%. After decanting and washing 2 times with PBS, it is blocked with 200 μl of BSA/PBS 3% during 12 hrs at 4° C., decanting and washing 2 times by immersion in PBS, adding 50 μl of commercial antibody anti-HA (conjugated with horseradish peroxidase) diluted 1:1,000 in BSA/PBS 1% and incubated 1 hour at 37° C. Decanting and washing with distilled water, the substrate is added: 50 μl of ABTS incubating at room temperature in dark to be read (405 nm).

Recognizing ELISA for TNFα. The immunoenzymatic assay ELISA is performed to find the clones that express a soluble VHNAR with affinity to TNFα ☐ using 50 μl of this cytokine (3 μg/ml in Sodium carbonate buffer 50 mM, pH: 9.4), incubating the overnight at 4° C., after washings and blocking, is added 100 μl of supernatant of each obtained clone to detect the VHNAR soluble molecules, incubating 2 hours at 37° C., washing and reveal with anti-HA antibodies conjugated with peroxidase, using ABTS as substrate, the reaction stops the peroxidase reaction by adding 50 μL of HCl 6 N, the change of color is observed reading the absorbance at 405 nm. The negative controls are the culture of the bacteria TOP10F' free of insert of VHNAR and also VHNAR without primary antibody, and secondary (anti-HA/HRP), one more control has only ABTS substrate.

Large scale $V_H$NAR expression. Beginning with 2 liters of the culture of the selected clone and on a large scale realices the expression and purification of $V_H$NAR from 2 L of culture of the clones selected of the following way: 15 ml of SB media+Carbencillin [100 μg/ml] with a colony of TOP10F/pComb3X-$V_H$NAR, is shaken to 300 rpm/37° C., after 5.5 hours 2 ml is transferred to two flasks of 2 Liters with 1 L of standard SB media each, and shaken at 300 rpm/37° C., for 5 hr 20 minutes reaches a $DO_{600}$=0.7 and to 5 hr 50 adds 2 ml of IPTG 0.5 M to each flask, shaking to 300 rpm/37° C. by a period of 20 hour. Extraction of $V_H$NAR from periplasma is realized by means of osmotic shock.

Nickel Affinity Chromatography $V_H$NAR Purification. The obtained product from the periplasmic extraction was transferred to a column charged with agarose resine Ni-NTA (1 ml) previously equilibrated with charge solution (imidazol 40 mM in PBS), the diluted pass 3 times through the column, and washed with the solution of imidazol 40 mM in PBS), eluting with the solution of imidazol 500 mM in PBS and dializing and collecting. The obtained chromatograms shown the time of elution of the fractions for the $V_H$NAR clone TNF43 at minute 36.

Example 2

Sequences of vNARS Anti-TNFα and Anti-VEGF

The purified proteins of reactive clones were sequenced in Seqxcel Laboratory (San Diego, Calif.). The mixture reaction was prepared following the suggested conditions, using the primer Ompseq, because the pCOMb3X vector have the complementary sequence for this oligonucleotide, the obtained sequences with Mac Vector 7.2.2 program. The obtained amino acid and nucleotide sequence for clones specific for TNFα are SEQ ID NO:1, SEQ ID NO:2, (for clone 43) SEQ ID NO:3 and SEQ ID NO:4, (for clone 65) of the List of Sequences.

The obtained amino acid and nucleotide sequences for *P. pastoris* expression system are SEQ ID NO:7 and SEQ ID NO:8, (for clone 43) of the List of sequences.

The obtained amino acid and nucleotide sequence for *E. coli* expression system are SEQ ID NO:9 and SEQ ID NO:10, (for clone 43) of the List of sequences.

The obtained amino acid and nucleotide sequence of the vNAR specific to VEGF are SEQ ID NO:5 and SEQ ID NO:6, (clone 13) of the List of sequences.

Example 3

Expression in *Pichia pastoris*

We used *Pichia pastoris* for the expression of vNAR clone 43, following the EasySelect *Pichia* Expression Manual (Invitrogen, USA). The pPICZαA vector and X-33 strain were used. The expression conditions were: Methanol 2% and 2 days of culture (30° C., 250 rpm). The vNAR clone 43 was purified with IMAC. The use of *Pichia pastoris* expression system improved the quantity of protein expressed, the processing, folding and post-translational modification in comparison with *E. coli*.

Example 4

In Vitro Characterization of vNAR Specific to TNF-α

Characterization of Anti-TNF-α Shark Sequences

The variable regions of anti-TNF-α shark sequences are small molecules that recognize the antigen through a variable domain which presents two complementary determinant regions (CDRs), which present high variability. The alignment of the sequences of the isolated clones that neutralizes the cytokine TNF-α were denominated TNF43 and TNF65 and are shown in FIG. 1.

Thermostability

The vNAR TNF43 was heated at 90° C. for 1 hour, serial aliquots at following times 5; 10; 20; 30; 40; 50; 60 minutes were taken. In order to analyze the ability of each aliquot to recognize TNF-α an ELISA assay was done as follows: 50 μl of TNF-α, at an initial concentration of 5 μg/ml, were added by triplicate in ELISA plate wells, the plate was incubated for 1 hour at 37° C. Then the plate was blocked with 150 μL of 3% BSA in 1X PBS and incubated for 1 hour at 37° C. After liquid discard, were added 50 μl of the previously heated protein vNAR clone TNF43; As negative control, instead of TNF-α, it was used BSA 1% in PBS 1X to be probed with every time aliquot. After rinses with Tween 0.05% in PBS 1X, the 2nd antibody was added. 50 uL of reagent Anti-HA diluted 1:1000 in BSA1%/PBS 1X was added, incubated 1 hour at 37° C., discarded, rinsed, revealed during 30 minutes with peroxidase reactive, and analyzed at absorbance at 405 nm. The thermostable characteristic of the vNAR makes them suitable for pharmaceutical uses. See FIG. 2.

Example 5

In Vitro Neutralizing Activity of vNAR Anti-TNFα

Figure 3:
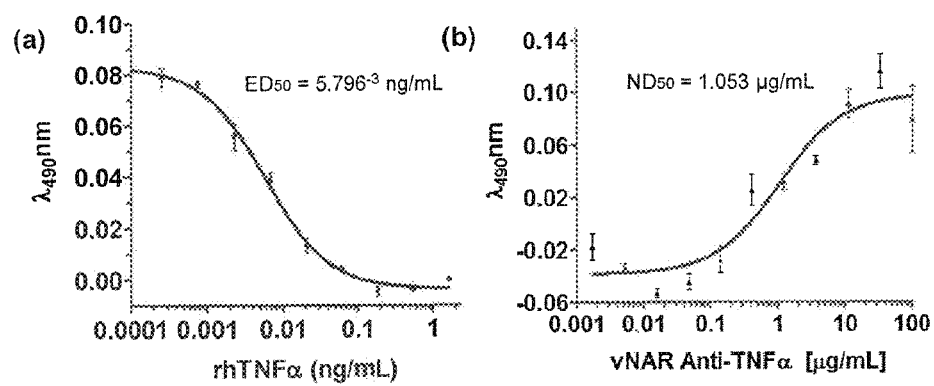
FIG. 3: Neutralizing activity of the recombinant protein VNAR anti TNF-α: a) Cytotoxic assay. Several dilutions of rhTNF-α cytokine were analyzed in order to identify the amount of cytokine required to produce effect in half of the culture cells. b) Neutralizing assay. It is identified the amount of recombinant antibody that produce neutralizing effect in half of the cell culture using 5ED50 rhTNF-α=$28.98^{-3}$ ng/mL. Results are given as the mean±SEM of 3 experiments.

In order to establish the 50 percent inhibitory dose ($DE_{50}$) for each one of $V_H$NAR anti-TNF-α clone, the cell line L929 of mice fibrosarcoma were used in presence of TNF-α being at 5 media Lethal Dose ($5DL_{50}$) previously determined. In a triplicate assay for each clone, 24,000 cells per well were grown incubated in a 96 plate during 6 hrs in conventional conditions with serial dilutions of $V_H$NAR anti-TNFα 100; 33.3; 11.1; 3.7; 1.2; 0.41; 0.13; 0.04; 0.015 μg/ml, and 1 μg/ml of actinomycin D, incubating during 18 hrs $CO_2$ 5%, 37° C. To measure cell survival first were added 20 μl/well of the reactive Cell Titer One, following incubation for 4 hrs and reading absorbance at 490 nm. See FIG. 3.

A probed F(ab)₂ anti-TNFα (Laboratorios Silanes) was used as reference curve of neutralization using the same concentrations as $V_H$NA proteins. As negative control the cells were grown but in absence of antibodies.

Example 6

In Vivo Evaluation of vNAR Specific for TNFα by Means of Sepsis Murine Model

The $V_H$NAR of invention in pharmaceutical formulations were evaluated in preclinical a sepsis model as follows:

1) endotoxic shock model (ChE), induced before the injection of lethal dose of lipopolysaccharide (LPS).
2) Through bacteria administration;
3) Through cecal ligation and puncture model (LyPC).

In the two first, there is a temporary stimulus that is eliminated when the antigens are depurated, however, this models has been useful to identify the role of cytokines such as TNF-α, IL-1, IL-8, IFNγ or IL-10 in sepsis and to explain the mechanisms mediated for said cytokines, among these mechanisms stand out: over production of nitric oxide, diminution of periferic vascular resistance, production of free radicals, intravascular disseminated coagulation.[11, 21]

Endotoxic shock mouse model. Mice Balb/c males of between 8-12 weeks of age were injected with endotoxin derived from *Escherichia coli* (LPS) intraperitoneal as a model for endotoxic shock. Control endotoxic animals received an $LD_{100}$ injection of LPS. Experimental animals received 1 mg/kg of the recombinant antibody 15 minutes prior to the LPS injection. Antibody administration was repeated 2 and 24 h after the LPS injection. Control animals received saline solution. Mouse mortality was monitored daily for 72 hours.

In the case of LyPC model it is allowed the entrance of intestinal bacteria (flora) to blood stream, although *E. coli* is the most common, frequently the most common is the polymicrobial infection unknowing the bacterial concentration and the time of staying in the blood stream. In this model there is a consistent presence of seric cytokines such as IL-1, IL-6, IL-8, IFNγ and IL-10; the cytokine TNFα is also found but is less consistent[18]

The biological activity has been determined through the administration of antibodies anti-TNFα in different stages of the infection and dosages.[11, 21]

Figure 4:
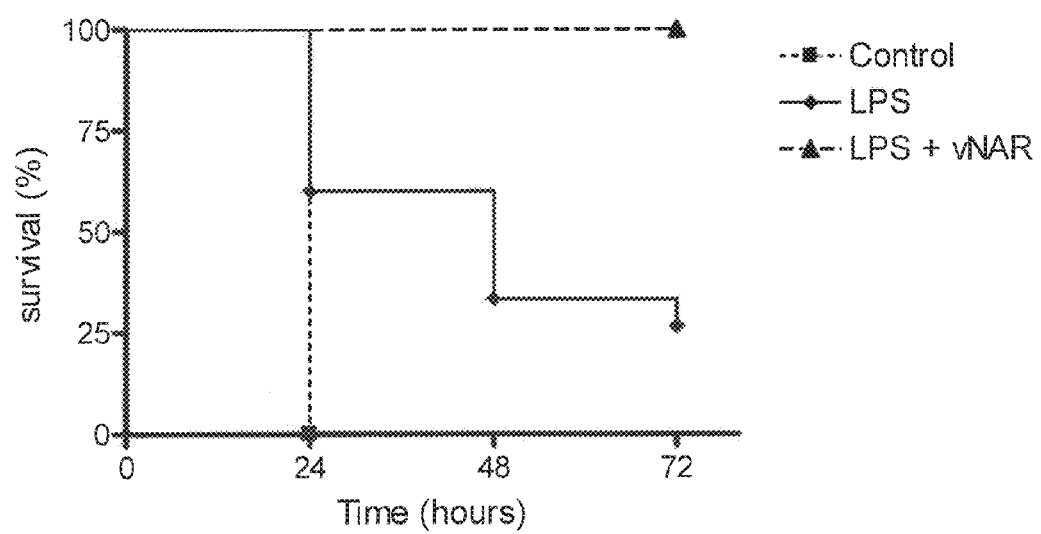
FIG. 4: Survival of mice treated with vNAR anti TNF-α in an LPS-induced septic shock model. Mice n=20 in each treatment group were analized. Mouse mortality was monitored for 72 h. 25% of the treated animals with recombinant antibody animals survive related to the control group (p<0.001).

In strict sense this endotoxemic model resembles an infection, in this model, the in vivo intravenous administration of Lipopolysaccharides (LPS) generates the production of TNFα directly associated with tissue damage and mortality, the protection conferred to administration of high doses of recombinant shark antibodies specifics for TNF-α, look for neutralization of circulating cytokine that permits consider this use as a treatment of inflammatory profiles.[22, 23] See FIG. 4.

Figure 5:
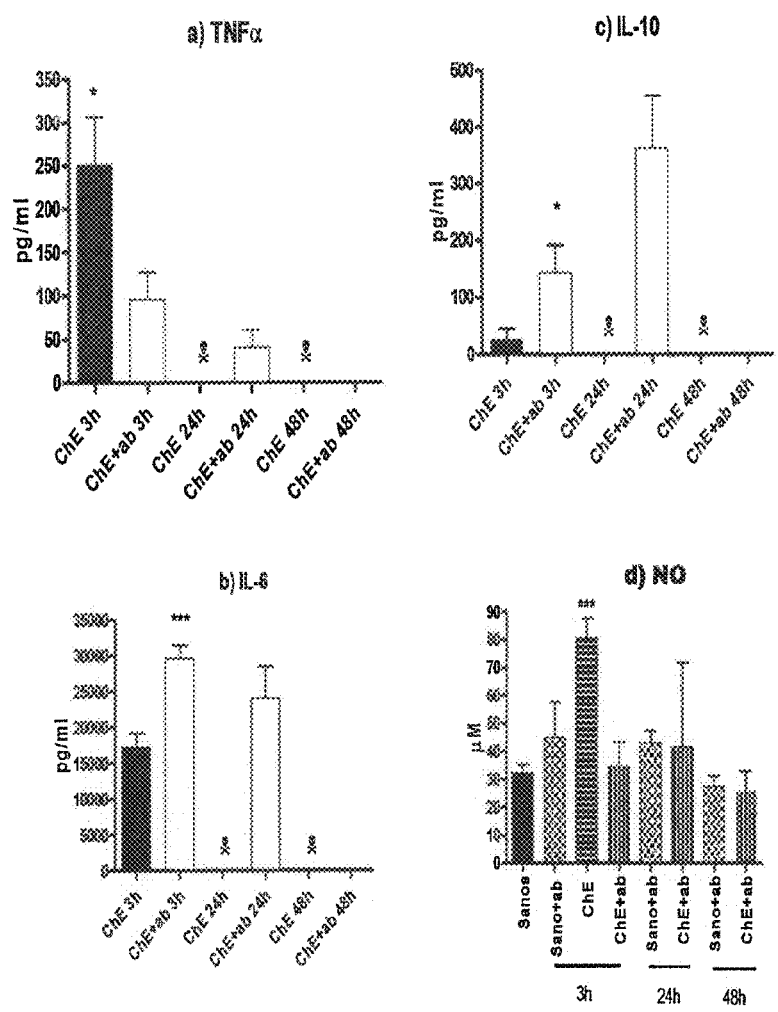
FIG. 5: Profile of serum cytokines and nitric oxide (NO) during the septic process. Serum samples were obtained from septic animals and the presence of cytokines at serial times was measured. Control or recombinant antibody vNAR anti TNFα were administered in serial times: 3, 24, 48 hrs, in endotoxic shock (ChE) conditions alone or with vNAR anti-TNFα (CHE+ab) as stated in legend. The differences between groups were determined using a one-way ANOVA test and a Mann-Whitney U test; with differences statistically significant (p<0.05) vs. control group, for the same time and treatment.

Measurement of serum cytokines and nitric oxide: Blood was extracted from mice after endotoxic shock and treatment by cardiac puncture. Levels of TNFα, IL1, IL6, IL-10, were determined through sandwich enzyme-linked immunosorbent assay (ELISA), using the commercial duoSet system (R&D Systems-USA) in accordance with the protocol suggested by the manufacturer. The levels of NO production in the sample was determined by assaying the stable end product NO2- by Greiss reaction using a commercial kit (Promega-USA). See FIG. 5.

The contribution of proinflammatory cytokines to lethality in the LPS endotoxin sepsis model has been well-established. The administration of 1 mg/kg of vNAR anti TNF was able to protect even after the septic process induced by LPS administration in a 25% using and $LD_{100}$ doses. These results suggest that the protective mechanism by decrease of the TNF and nitric oxide.

Example 7

In Vitro Characterization of the vNAR Specific to VEGF

Neutralization Assays of $VEGF_{165}$ with $V_HNAR$ in HUVEC Cells:

In order to obtain the media inhibitory dosage ($DI_{50}$) for each of the clones $V_HNAR$ anti-$VEGF_{165}$, HUVEC cells were grown, 5000/well in a 96 plate with collagen (16 μg/mL) in M199 incomplete media and 3 effective media doses (3DE50) of VEGF165. The plate was incubated during 2 hrs in conventional conditions, then were added a volume of 100 μl of serial dilutions of vNAR anti-$VEGF_{165}$ in incomplete media, as follows: 600; 300; 100; 33.3; 11.1; 3.7; 1.2; 0.41; 0.13; 0.04 and 0.015 μg/ml. The plated were incubated during 96 hrs in conventional conditions ($CO_2$ 5%, 37° C., in wet atmosphere), then were added 20 μl/well of the reactive for cellular titration and incubated for 4 hrs, reading absorbance at 490 nm.

A probed $F(ab)_2$ anti-$VEGF_{165}$ (Laboratorios Silanes) was used as reference curve of neutralization using the same concentrations as vNARs proteins. As negative control in was used HUVEC cells in absence of antibodies anti-VEGF. The resultant reactive clone capable to block VEGF activity was isolated (named VEGF13), it is required 2.37 μg/ml to neutralize $3ED_{50}$ (6 ng/ml) of $rhVEGF_{165}$. (1 $ED_{50}$=2 ng/ml). The results are shown in Table II:

TABLE II

|  | F(ab')$_2$ control | VEGF13 |
|---|---|---|
| $DI_{50}$(μg/mL) | 3.68 | 2.37 |
| $R^2$ | 74.18% | 11.29% |
| Degree of freedom | 29 | 26 |
| Value | 33 | 30 |

Example 8

In Vivo Efficacy Study: Performance of vNAR Protein Anti-VEGF in Hypoxic Retinopathy in Newborn Mice In order to evaluate in vivo efficacy of the vNAR specific for VEGF (clone 13 SEQ ID NO:5), we used an hypoxic retinopathy induction model where an increase in ocular tissue vascularization occurs, as follows: Forty C-57-B6 strain newborn mice were set apart in 4 groups including 10 mice each. 3 groups received different doses of the active ingredient (1 μg/mL, 0.5 μg/mL and 0.01 μg/mL), and 1 group received placebo. Thereafter, they were put in a normo oxemic environment and received one of the different doses of anti-VEGF vNAR or placebo three every 6 hours during 7 days. It has been described that VEGF associated retinal vascular proliferation occurs.

One day after study treatment ends and before performing euthanasia, both eyeballs were enucleated to carry out an immune-histopathological analysis to determine the level of neovascularization in the vNAR treated retina as compared to placebo treated retina. The number of neovascular cells formed in the periphery of the ocular tissue were obtained through an histopathological evaluation.

Figure 6:
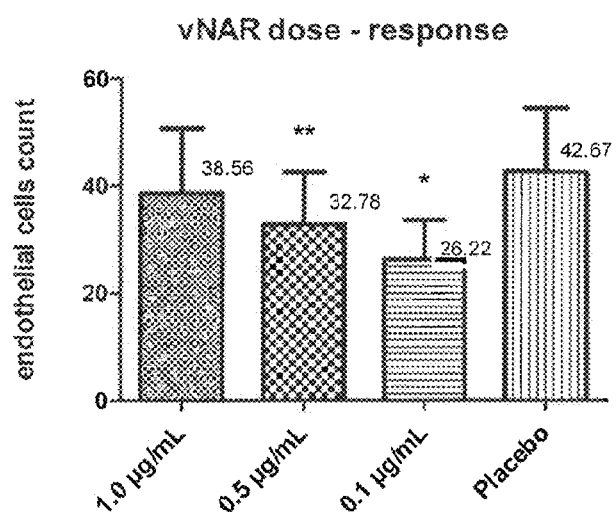
FIG. 6: Protective effect of serial doses of vNAR anti-VEGF compared with placebo over the endothelial cell proliferation of the retina.

The microscopic examination of the different enucleated eyes, were evaluated with routine stains (hematoxylin & eosin and periodic acid-Schiff "PAS"). The counted endothelial cells were those located between ganglion cell layer and the vitreous below the inner limiting membrane. The total number of endothelial cells was calculated in 10 high-power-fields (×40). The endothelial cells attached to the posterior capsule of the lens (tunica vasculosa lentis remnants) and all of those located in other layers of the sensory retina were not included. We can conclude that, 1) vNAR penetrate the eye and reaches the retina where it exerts its antiproliferative response, 2) the biological effect is dose dependent. See FIG. 6.

Example 9

Evaluation of Intraocular Penetration of the vNARs

In order to determine the pharmacokinetics profile of vNARs administered topically to rabbits, a study was designed to evaluate its ocular penetration: 6 New Zealand adult rabbits weighing between 2 to 2.5 kg received a eye drops of vNAR at a concentration of 0.1 µg/ml. Each rabbit received the vNAR solution every 20 minutes during 10 hours. The eyedrops were administered right at the center of the corneal surface. One rabbit was euthanized at each timepoint: 3, 5, 8, 10, and 24 hours. One rabbit did not receive any vNAR and was a negative control.

Samples of aqueous humor (0.1 ml) were collected and further analyzed by an ELISA to determine the vNAR concentration. See FIG. 7.

Figure 7:
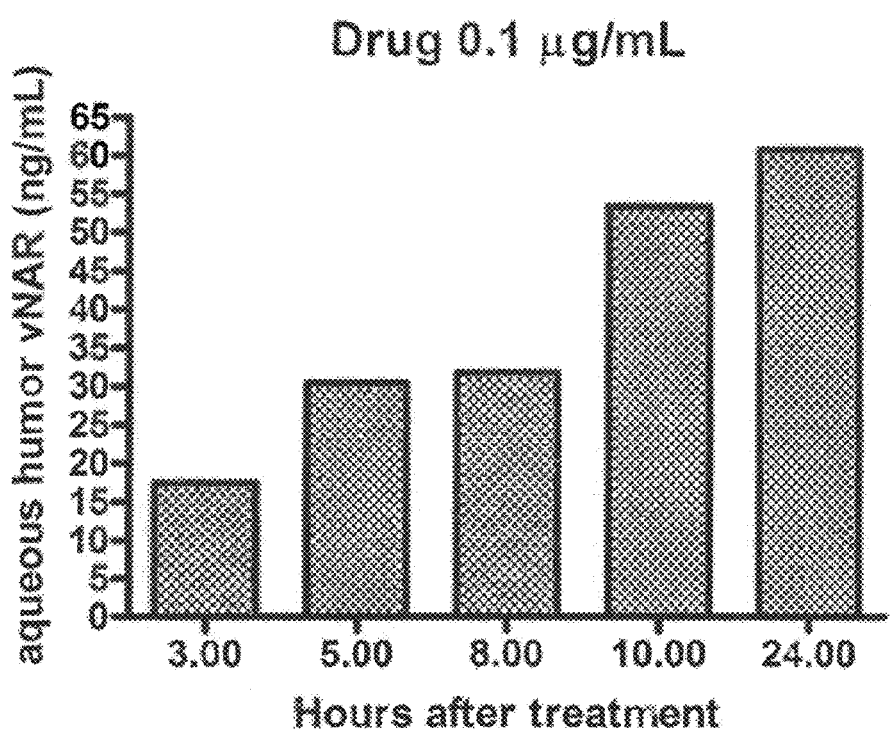
FIG. 7: Recombinant antibody levels. The drug was administered every 20 minutes during 10 hours. Samples of aqueous humor were collected at different time points: The amount of protein was measured by ELISA. a) Study drug 0.1 µg/ml.

The results shown in graphic a) of FIG. 7 the detection of the protein increase gradually until reach 60.68 mg/mL. In this case the penetration correlates directly with the progressive increase of the drug.

The single chain recombinant antibody vNAR showed penetration through the rabbit cornea after 3 hours of topical administration, this feature also makes them suitable molecules for clinical use, specially for topic administration, including topic ophthalmic use.

All statistical analyses were performed using GraphPad Prism 4 software. The differences among groups were determined using a one-way ANOVA test and a Mann-Whitney U test; they were considered significant when $p<0.05$ vs. control.

REFERENCES

1. Nuttall S D, et al. Isolation of the new antigen receptor from wobbegong sharks, and use as a scaffold for the display of protein loop libraries. Mol Immunol. 2001 August; 38(4): 313-26.
2. Dumoulin M., et al. Single-domain antibody fragments with high conformational stability. Protein Science, 2002. 11: 500-515.
3. Flajnik Martin F. et al. Mutational pattern of the nurse shark antigen receptor gene (NAR) is similar to that of mammalian Ig genes and to spontaneous mutations in evolution: the translesion synthesis model of somatic hypermutation. International Immunology, 1999. 11(5):825-833.
4. Muyldermans, S. and Lauwereys M. Unique single-domain antigen binding fragments derived from naturally occurring camel heavy-chain antibodies. Journal Molecular Recognition, 1999. 12:131-140.
5. Nuttall S D, et al. Isolation and characterization of an IgNAR variable domain specific for the human mitochondrial translocase receptor Tom70. Eur. J. Biochem, 2003. 270: 3543-3554.
6. Nuttall S D, et al. A naturally occurring NAR variable domain binds the Kgp protease from *Porphyromonas gingivalis*. FEBS Lett. 2002, 10; 516(1-3):80-6.
7. Nuttall S D, et al. Selection and affinity maturation of IgNAR variable domains targeting *Plasmodium falciparum* AMA1. Proteins. 2004, 1; 55 (1):187-97.
8. Dooley H, et al. Selection and characterization of naturally occurring single-domain (IgNAR) antibody fragments from immunized sharks by phage display. Mol Immunol. 2003 September; 40(1):25-33.
9. Green, R. S. et al. Canadian Association of Emergency Physicians Sepsis Guidelines: The optimal management of severe sepsis in Canadian emergency departments. CJEM. 2008 September; 10 (5):443-59.
10. Angus D C, et al. Epidemiology of severe sepsis in the United States: analysis of incidence, outcome, and associated costs of care. Crit Care Med 2001. 29: 1303-1310.
11. Bochud P Y, Calandra T. Pathogenesis of sepsis: new concepts and implications for future treatment. BMJ 2003. 326: 262-266.
12. Gérard C, et al. Interleukin 10 reduces the release of tumor necrosis factor and prevents lethality in experimental endotoxemia. J Exp Med 1993; 177: 547-550.
13. Wenzel R P, Pinsky M R, Ulevitch R J and Young L. Current understanding of sepsis. CID 1996; 22: 407-413.
14. Echeverri M M A. et al. Nuevos avances de la terapia biológica en la psoriasis. Med. Cutan. Iber. Lat. Am. 2005; 33 (1): 7-17.
15. EMEA [sitio interne] http://www.emea.europa.eu/humandocs/PDFs/EPAR/Enbrel/emea-combined-h262es.pdf
16. Dutz, J P et al. Psoriasis and pustular dermatitis triggered by TNF-{alpha} inhibitors in patients with rheumatologic conditions. Arch Dermatol. 2007 February; vol 143(2): 223-31. Review.
17. Duran Gimenez-Rico, et al. Sepsis y shock séptico: un torbellino de mediadores inflamatorios de dificil manejo terapéutico. *An. Med. Interna (Madrid)*. 2002, vol. 19(1): 35-43.
18. Feldmann M. et al. ANTI-TNFα THERAPY OF RHEUMATOID ARTHRITIS: What Have We Learned. Annual Review of Immunology. 2001; Vol. 19: 163-196.
19. Maharaj A: and Dámore P. Roles for VEGF in adult. Microvasc. Res. 2007; 74(2-3):100-113.
20. Hendriksen, E. M. et al. Angiogenesis, http://www.sciencedirect.com/science?ob=ArticleURL&_udi=B6WN8-4V3HFJV-1&_user=8467320&_coverDate=03%2F31%2F2009&_alid=1517958129&_rdoc=17&_fmt=high&_orig=search&_origin=search&_zone=slt_list_item&_cdi=6956&_sort=r&_st=4&_docanchor=&_ct=23921&_acct=C000091209&_version=1&_urlVersion=0&_userid=8467320&md5=0ca10b9dc464ec7648dfc135dcfce2cb&searchtype=a-hit2 hypoxia and VEGF expression during tumour growth in a human xenograft tumour model. Microvascular Research, 2009; Vol. 77(2): 96-103.
21. Stone J, et al. Development of retinal vasculature is mediated by hypoxia-induced vascular endothelial growth factor (VEGF) expression by neuroglia. J Neurosci. 1995 July; 15 (7 Pt 1):4738-47.
22. Witmer A N, et al. Vascular endothelial growth factors and angiogenesis in eye disease. Prog Retin Eye Res. 2003; 22(1):1-29.
23. Ebong S, Call D, Nemzek J, Bolgos G, Newcomb D and Remick D. Immunopathologic alterations in murine models of sepsis of increasing severity. Infect Immun 1999. 67: 6603-6610.
24. Coleman H. R. et al. Age-related macular degeneration. Lancet. 2008 November 22; 372(9652): 1835-1845.

What is claimed is:

1. An isolated vNAR protein comprising an amino acid sequence SEQ NO:1 or a functional variant thereof with a sequence identity of at least 95%, characterized in that the protein binds to tumor necrosis factor α (INFα).

2. The isolated vNAR protein of claim 1, wherein the amino acid sequence or functional variant thereof contains the following amino acid residues: the amino acid residue 28 is one of Ile or Asn, the amino acid residue 33 is one of Ser or Asn, the amino acid residue 75 is one of Phe or Val, the amino acid residue 88 is one of Thr, Ala or Glu, the amino acid residue 89 is one of Ser or Thr, the amino acid residue 90 is one of Gly, Asp or Ser, and the amino acid residue 91 is one of Tyr or Gly.

3. The isolated vNAR protein of claim 1, comprising the amino acid sequence SEQ ID NO:1.

4. The isolated vNAR protein of claim 1, wherein the TNFα is human TNFα.

5. The isolated vNAR protein of claim 1, prepared by a process comprising immunizing a shark with TNFα.

6. A method for treating sepsis, septic shock, psoriasis, arthritis rheumatoid, eye inflammation, or corneal transplant rejection in a subject, comprising administering to said subject an effective amount of a vNAR protein of claim 1.

7. A pharmaceutical composition that comprises a vNAR protein of claim 1, and a pharmaceutically acceptable carrier.

8. The pharmaceutical composition of claim 7, wherein the TNFα is human TNFα.

9. The pharmaceutical composition of claim 7, wherein the isolated vNAR protein is prepared by a process comprising immunizing a shark with TNFα.

10. An isolated vNAR protein comprising an amino acid sequence SEQ ID NO:3 or a functional variant thereof with a sequence identity of at least 95%, characterized in that the protein binds to TNFα.

11. The isolated vNAR protein of claim 10, comprising the amino acid sequence SEQ ID NO:3.

12. The isolated vNAR protein of claim 10, wherein the TNFα is human TNFα.

13. The isolated vNAR protein of claim 10, prepared by a process comprising immunizing a shark with TNFα.

14. A method for treating sepsis, septic shock, psoriasis, arthritis rheumatoid, eye inflammation, or corneal transplant rejection in a subject, comprising administering to said subject an effective amount of a vNAR protein of claim 10.

15. A pharmaceutical composition that comprises a vNAR protein of claim 10, and a pharmaceutically acceptable carrier.

16. The pharmaceutical composition of claim 15, wherein the TNFα is human TNFα.

17. The pharmaceutical composition of claim 15, wherein the isolated vNAR protein is prepared by a process comprising immunizing a shark with TNFα.

18. An isolated vNAR protein comprising an amino acid sequence SEQ ID NO:7 or a functional variant thereof with a sequence identity of at least 95%, characterized in that the protein binds to TNFα.

19. The isolated vNAR protein of claim 18, comprising the amino acid sequence SEQ ID NO:7.

20. The isolated vNAR protein of claim 18, wherein the TNFα is human TNFα.

21. The isolated vNAR protein of claim 18, prepared by a process comprising immunizing a shark with TNFα.

22. A method for treating sepsis, septic shock, psoriasis, arthritis rheumatoid, eye inflammation, or corneal transplant rejection in a subject, comprising administering to said subject an effective amount of a vNAR protein of claim 18.

23. A pharmaceutical composition that comprises a vNAR protein of claim 18, and a pharmaceutically acceptable carrier.

24. The pharmaceutical composition of claim 23, wherein the TNFα is human TNFα.

25. The pharmaceutical composition of claim 23, wherein the isolated vNAR protein is prepared by a process comprising immunizing a shark with TNFα.

26. An isolated vNAR protein comprising an amino acid sequence SEQ NO:9 or a functional variant thereof with a sequence identity of at least 95%, characterized in that the protein binds to TNFα.

27. The isolated vNAR protein of claim 26, comprising the amino acid sequence SEQ ID NO:9.

28. The isolated vNAR protein of claim 26, wherein the TNFα is human TNFα.

29. The isolated vNAR protein of claim 26, prepared by a process comprising immunizing a shark with TNFα.

30. A method for treating sepsis, septic shock, psoriasis, arthritis rheumatoid, eye inflammation, or corneal transplant rejection in a subject, comprising administering to said subject an effective amount of a vNAR protein of claim 26.

31. A pharmaceutical composition that comprises a vNAR protein of claim 26, and a pharmaceutically acceptable carrier.

32. The pharmaceutical composition of claim 31, wherein the TNFα is human TNFα.

33. The pharmaceutical composition of claim 31, wherein the isolated vNAR protein is prepared by a process comprising immunizing a shark with TNFα.

* * * * *